(12) United States Patent
DeSimone et al.

(10) Patent No.: US 6,906,075 B2
(45) Date of Patent: Jun. 14, 2005

(54) MELANIN CONCENTRATING HORMONE RECEPTOR LIGANDS: SUBSTITUTED BENZOIMIDAZOLE ANALOGUES

(75) Inventors: Robert W. DeSimone, Durham, CT (US); Cheryl Steenstra, Meriden, CT (US); Linda Gustavson, Guilford, CT (US); Rajagopal Bakthavatchalam, Madison, CT (US); Alan Hutchison, Madison, CT (US)

(73) Assignee: Neurogen Corp., Branford, CT (US)

( * ) Notice: Subject to any disclaimer, the term of this patent is extended or adjusted under 35 U.S.C. 154(b) by 58 days.

(21) Appl. No.: 10/339,111

(22) Filed: Jan. 9, 2003

(65) Prior Publication Data

US 2003/0216390 A1 Nov. 20, 2003

Related U.S. Application Data

(60) Provisional application No. 60/347,279, filed on Jan. 10, 2002.

(51) Int. Cl.⁷ ................... C07D 401/10; A61K 31/445; A61K 31/495

(52) U.S. Cl. ................. 514/254.01; 514/323; 514/399; 544/370; 546/201; 548/306.1

(58) Field of Search ............... 548/306.1; 514/399, 514/254.01, 323; 546/201; 544/370

(56) References Cited

U.S. PATENT DOCUMENTS

| 6,271,241 B1 | 8/2001 | DeSimone et al. |
| 6,358,949 B1 | 3/2002 | DeSimone et al. |
| 6,380,210 B1 | 4/2002 | DeSimone et al. |

FOREIGN PATENT DOCUMENTS

| EP | 1254668 | 11/2002 |
| GB | 1115390 | 5/1968 |
| JP | 09-124609 | 5/1997 |
| JP | 2001-226269 | 8/2001 |
| WO | WO 00/59886 | 10/2000 |
| WO | WO 00/59887 | 10/2000 |
| WO | WO 00/59905 | 10/2000 |
| WO | WO 01/00611 | 1/2001 |
| WO | WO 01/21169 | 3/2001 |
| WO | WO 01/21577 | 3/2001 |
| WO | WO 01/82925 | 11/2001 |
| WO | WO 01/87834 | 11/2001 |
| WO | WO 02/02744 | 1/2002 |
| WO | WO 02/04433 | 1/2002 |
| WO | WO 02/06245 | 1/2002 |
| WO | WO 02/28839 | 4/2002 |
| WO | WO 02/50062 | 6/2002 |
| WO | WO 02/051809 | 7/2002 |
| WO | WO 02/057233 | 7/2002 |
| WO | WO 02/076929 | 10/2002 |
| WO | WO 02/076947 | 10/2002 |
| WO | WO 02/083134 | 10/2002 |
| WO | WO 02/089729 | 11/2002 |
| WO | WO 02/092575 | 11/2002 |
| WO | WO 03/004027 | 1/2003 |

Primary Examiner—Joseph K. McKane
Assistant Examiner—Golam M M Shameem
(74) Attorney, Agent, or Firm—Ann T. Kadlecek; Seth A. Fidel

(57) ABSTRACT

Melanin concentrating hormone receptor ligands (especially substituted benzoimidazole analogues), capable of modulating MCH receptor activity, are provided. Such ligands may be used to modulate MCH binding to MCH receptors in vivo or in vitro, and are particularly useful in the treatment of a variety of metabolic, feeding and sexual disorders in humans, domesticated companion animals and livestock animals. Pharmaceutical compositions and methods for treating such disorders are provided, as are methods for using such ligands for detecting MCH receptors (e.g., receptor localization studies).

16 Claims, No Drawings

SEQUENCE LISTING

<160> NUMBER OF SEQ ID NOS: 4

<210> SEQ ID NO 1
<211> LENGTH: 1114
<212> TYPE: DNA
<213> ORGANISM: Macaca fascicularis

<400> SEQUENCE: 1

```
gagcaggcga ccggcactgg ctggatggac ctggaagcct cgctgctgcc cactggtccc        60
aacaccagca acacctctga tggccccgat aacctcacct cggcaggatc acctcctcgc       120
tcagggagcg tctcctacat caacatcatc atgccttcgg tgttcggcac catctgcctc       180
ctgggcatca tcgggaactc catggtcatc ttcgcggtcg tgaagaagtc caagctgcac       240
tggtgcaaca atgtccccga catcttcatc atcaacctct cggtggtgga tctcctcttt       300
ctcctgggca tgccttcat gatccaccag ctcatgggca atggggtgtg gcactttggg       360
gagaccatgt gcaccctcat cacggccatg gatgccaata gtcagttcac cagcacctac       420
atcctgaccg ccatggccat tgaccgctac ctggccaccg tccacccat ctcttccaca       480
```

```
aagttccgga agccctctgt ggccacccctg gtgatctgcc tcctgtgggc cctctccttc    540
atcagcatca cccccgtgtg gttgtatgcc agactcatcc ccttcccagg aggtgcagtg    600
ggctgcggca tccgcttgcc caacccggac actgaccttt actggttcac cctgtaccag    660 ttttcctgg cctttgccct gcccttcgtg gtcatcacgg ccgcatacgt gaggatcctg    720
cagcgcatga cgtcctcagt ggcccccgcc tcccagcgca gcatccggct gcggacaaag    780
agggtgaccc gcacagccat cgccatctgc ctggtcttct ttgtgtgctg ggcaccctac    840
tatgtgctac agctgaccca gttgtccatc agccgcccga ccctcacctt tgtctacctg    900
tacaatgcgg ccatcagctt gggctacgcc aacagctgcc tcaacccctt tgtgtacatt    960
gtgctctgcg agacgttccg caaacgcttg gtcctttcgg tgaagcctgc agcccagggg   1020
cagcttcgcg ctgtcagcaa cgctcagacg gctgacgagg agaggacaga aagcaaaggt   1080
acctgatact tcccctgcca ccctgcacac ctcc                                1114
```

<210> SEQ ID NO 2
<211> LENGTH: 353
<212> TYPE: PRT
<213> ORGANISM: Macaca fascicularis

<400> SEQUENCE: 2

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
```

-continued

```
                260                 265                 270
Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
        290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr

<210> SEQ ID NO 3
<211> LENGTH: 24
<212> TYPE: DNA
<213> ORGANISM: Homo sapiens

<400> SEQUENCE: 3
gagcaggcga ccggcactgg ctgg                                             24

<210> SEQ ID NO 4
<211> LENGTH: 28
<212> TYPE: DNA
<213> ORGANISM: Homo sapiens

<400> SEQUENCE: 4
ggaggtgtgc agggtggcag gggaagta                                         28
```

MELANIN CONCENTRATING HORMONE RECEPTOR LIGANDS: SUBSTITUTED BENZOIMIDAZOLE ANALOGUES

CROSS REFERENCE TO RELATED APPLICATIONS

This application claims priority to U.S. Provisional Application No. 60/347,279, filed Jan. 10, 2002.

FIELD OF THE INVENTION

This invention relates generally to substituted benzoimidazole analogues that are modulators of melanin concentrating hormone receptors, and to the use of such compounds for treating a variety of metabolic, eating and sexual disorders. The invention further relates to the use of such compounds as probes for the detection and localization of MCH receptors.

DESCRIPTION OF THE SEQUENCE LISTING

SEQ ID NO:1 Cynomolgus macaque MCH1R DNA sequence

SEQ ID NO:2 Cynomolgus macaque MCH1R amino acid sequence

SEQ ID NO:3 Forward cloning primer

SEQ ID NO:4 Reverse cloning primer

BACKGROUND OF THE INVENTION

Melanin concentrating hormone, or MCH, is a cyclic 19 amino acid neuropeptide that functions as a regulator of food intake and energy balance. MCH is produced in the hypothalamus of many vertebrate species, including humans, and serves as a neurotransmitter in the lateral and posterior hypothalamus. Both of these regions are associated with behaviors such as eating, drinking, aggression and sexual behavior. MCH is also produced at various peripheral sites, including the gastrointestinal tract and testis.

The postulated role of MCH in feeding behavior and body weight is confirmed by the finding that i.c.v. injection of MCH into the lateral ventricle of the hypothalamus increases caloric consumption in rats over similarly treated control animals. Furthermore, rats having the ob/ob genotype exhibit a 50–80% increase in MCH mRNA expression as compared to leaner ob/+ genotype mice. MCH knockout mice are leaner than genetically identical, but normal MCH-producing mice due to hypophagia and an increased metabolic rate.

MCH activity is mediated via binding to specific receptors. Like other G protein-coupled receptors (e.g., neuropeptide Y (NPY) and beta-adrenergic receptors), MCH receptors are membrane-spanning proteins that consist of a single contiguous amino acid chain comprising an extracellular N-terminal domain, seven membrane-spanning alpha helical domains (connected by three intracellular loop domains alternating with three extracellular loop domains), and an intracellular C-terminal domain. Signal transduction is initiated by the binding of MCH to the receptor. This elicits conformational changes in the extracellular domains. When the receptor is functioning properly, these conformational changes propagate through the transmembrane domains and result in a coordinated change in the intracellular portions of the receptor. This precise alteration in the intracellular domains acts to trigger the associated G-protein complex to modulate intracellular signaling.

The MCH type 1 receptor (MCH1R) is a 353 amino acid, 7-transmembrane, alpha-helical, G-coupled protein receptor, first reported as orphan receptor SLC-1 Kolakowski et al. (1996) FEBS Lett. 398:253–58 and Lakaye et al. (1998) Biochim. Biophys. Acta 1401:216–220. Chambers et al. (1999) Nature 400:261–65 and Saito et al. (1999) Nature 400:265–69 then showed SLC-1 to be an MCH receptor. Immunohistochemistry studies of rat brain sections indicate that the MCH1R is widely expressed in brain. MCH1R expression is found in olfactory tubercle, cerebral cortex, substantia nigra, basal forebrain CA1, CA2, and CA3 field of the hippocampus, amygdala, and in nuclei of the hypothalamus, thalamus, midbrain and hindbrain. Strong signals are observed in the ventromedial and dorsomedial nuclei of the hypothalamus, two areas of the brain involved in feeding behavior. Upon binding MCH, MCH1R expressed in HEK 293 cells mediate a dose-dependent release of intracellular calcium. Cells expressing MCH1R also exhibit a pertussis toxin sensitive dose-dependent inhibition of forskolin-elevated cyclic AMP, indicating that the receptor couples to a $G_{i/o}$ G-protein alpha subunit.

Recently, a second MCH receptor (MCH2R) was identified (WO 01/70975; WO 01/07606; WO 00/49046; An et al., Proc. Natl. Acad. Sci. USA (2001) 98:7576–7581; Sailer et al., Proc. Natl. Acad. Sci. USA (2001) 98:7564–7569; Hill et al., J. Biol. Chem. (2001) 276:20125–20129; Mori et al., Biochem. Biophys. Res. Commun. (2001) 283:1013–1018). MCH2R has an overall amino acid identity of more than 30% with MCHR1, and is detected specifically in most regions of the brain, with an expression pattern similar to that of MCHR1.

Because MCH is an important regulator of food intake and energy balance, agents capable of modulating the activity of MCH receptors, especially MCHR1, are highly desirable for the treatment of obesity, eating disorders (e.g., bulimia and anorexia), sexual disorders (e.g., anorgasmic or psychogenic impotence) and metabolic disorders, such as diabetes. Small molecule, non-peptide antagonists of MCH receptors would be of particular value for such therapies. The present invention fulfills this need, and provides further related advantages.

SUMMARY OF THE INVENTION

The present invention provides MCH receptor modulators that inhibit or enhance MCH binding to MCH receptor. More specifically, within certain aspects, compounds provided herein are characterized by one of the following formulas:

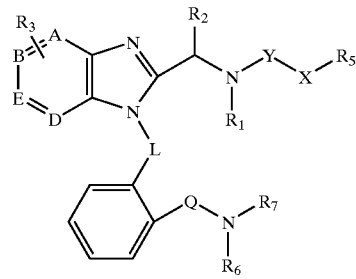

-continued

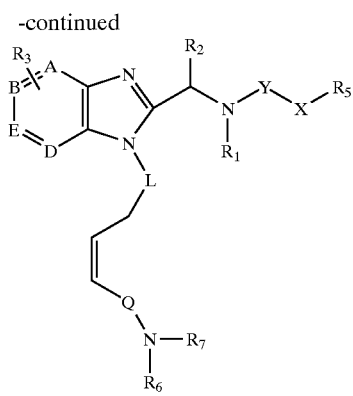

or a pharmaceutically acceptable salt thereof, wherein:

A, B, E and D each independently represent CH or N, with the proviso that not more than two of A, B, E and D represent N;

$R_1$ is: (i) hydrogen, —C(=O)—NH$_2$, —SO$_2$NH$_2$, or —COOH; (ii) C$_1$–C$_8$alkyl, C$_2$–C$_2$–C$_8$alkenly, C$_2$–C$_8$alkynyl, C$_2$–C$_8$alkanoyl, C$_2$–C$_6$alkyl ether, C$_1$–C$_8$alkylthio, mono- or di-(C$_1$–C$_8$alkyl)amino, mono- or di-(C$_1$–C$_8$alkyl)sulfonamido, or mono- or di-(C$_1$–C$_8$alkyl)carboxamido, each of which is optionally substituted with from 1 to 9 substituents independently selected from hydroxy, halogen, amino, cyano, nitro, C$_1$–C$_8$alkyl and haloC$_1$–C$_8$alkyl and mono- and di-(C$_1$–C$_8$alkyl)amino; or (iii) joined with $R_2$ to form a 5- to 7-member heterocyclic ring, optionally substituted with from 1 to 3 substituents independently selected from hydroxy, halogen, amino, cyano, nitro, C$_1$–C$_8$alkyl and haloC$_1$–C$_8$alkyl;

$R_2$ is: (i) hydrogen, —C(=O)—NH$_2$, —SO$_2$NH$_2$, or —COOH; (ii) C$_1$–C$_8$alkyl, C$_2$–C$_8$alkynyl, C$_2$–C$_8$alkynyl, C$_1$–C$_8$alkoxy, C$_2$–C$_8$alkanoyl, C$_2$–C$_8$alkyl ether, C$_2$–C$_8$alkanoyloxy, C$_1$–C$_8$alkoxycarbonyl, C$_1$–C$_8$)carbonate, C$_1$–C$_8$alkylthio, mono- or di-(C$_1$–C$_8$alkyl)amino, C$_1$–C$_8$carbamate, mono- or di-(C$_1$–C$_8$alkyl)sulfonamido or mono- or di-(C$_1$–C$_8$alkyl)carboxamido, each of which is optionally substituted with from 1 to 9 substituents independently selected from hydroxy, halogen, amino, cyano, nitro, C$_1$–C$_8$alkyl and haloC$_1$–C$_8$alkyl; or (iii) joined with $R_1$ to form a 5- to 7-member heterocyclic ring, optionally substituted with from 1 to 3 substituents independently selected from hydroxy, halogen, amino, cyano, nitro, C$_1$–C$_8$alkyl and haloC$_1$–C$_8$alkyl;

$R_3$ represents 0 to 4 substituents, wherein each substituent is linked to a carbon atom at A, B, E or D, and each substituent is independently selected from: (i) halogen, hydroxy, amino, cyano, nitro, —C(=O)—NH$_2$, —SO$_2$NH$_2$, and —COOH; and (ii) C$_1$–C$_8$alkyl, C$_2$–C$_8$alkenyl, C$_2$–C$_8$alkynyl, C$_1$–C$_8$alkoxy, C$_2$–C$_8$alkanoyl, C$_2$–C$_8$alkanoyloxy, C$_1$–C$_8$alkoxycarbonyl, C$_1$–C$_8$carbonate, C$_1$–C$_8$alkylthio, mono- and di-(C$_1$–C$_8$alkyl)amino, C$_1$–C$_8$carbamate, mono- and di-(C$_1$–C$_8$alkyl)sulfonamido, and mono- and di-(C$_1$–C$_8$alkyl)carboxamido, each of which is optionally substituted with from 1 to 9 secondary substituents independently selected from hydroxy, halogen, amino, cyano, nitro, C$_1$–C$_8$alkyl and haloC$_1$–C$_8$alkyl;

L is C$_1$–C$_3$alkyl;

Q is C$_0$–C$_3$alkyl, C$_2$–C$_3$alkenyl or C$_2$–C$_3$alkynyl;

X represents C$_0$–C$_3$alkyl, C$_2$–C$_3$alkenyl, C$_2$–C$_3$alkynyl, C$_1$–C$_3$alkoxy, C$_1$–C$_3$alkoxycarbonyl or C$_1$–C$_3$alkylthio;

Y is CH$_2$, —(C=O)—, —C(=S)—, —S(=O)— or —(SO$_2$)—;

$R_5$ represents an aromatic carbocyclic or heterocyclic group having from 1 to 3 fused or pendant rings, each ring containing from 5 to 8 ring members, wherein the aromatic group is optionally substituted by from 1 to 9 substituents that are independently selected from: (i) halogen, hydroxy, amino, cyano, nitro, —C(=O)—NH$_2$, —SO$_2$NH$_2$, and —COOH; and (ii) C$_1$–C$_8$alkyl, C$_2$–C$_8$alkenyl, C$_2$–C$_8$alkynyl, C$_1$–C$_8$alkoxy, C$_2$–C$_8$alkanoyl, C$_2$–C$_8$alkanoyloxy, C$_1$–C$_8$alkoxycarbonyl, C$_1$–C$_8$carbonate, C$_1$–C$_8$alkylthio, mono- and di-(C$_1$–C$_8$alkyl)amino, C$_1$–C$_8$carbamate, mono- and di-(C$_1$–C$_8$alkyl) sulfonamido, and mono and di-(C$_1$–C$_8$alkyl) carboxamido, each of which is optionally substituted with from 1 to 9 secondary substituents independently selected from hydroxy, halogen, amino, cyano, nitro, C$_1$–C$_8$alkyl and haloC$_1$–C$_8$alkyl; and $R_6$ and $R_7$ each independently represent optionally substituted C$_1$–C$_8$alkyl, or $R_6$ and $R_7$ jointly with the nitrogen atom to which they are bound form an optionally substituted 3 to 7 member heterocyclic ring. Optional substitutions for $R_6$ and $R_7$ occur at from 1 to 3 positions, with each substituent independently selected from hydroxy, halogen, amino, cyano, nitro, C$_1$–C$_8$alkyl, haloC$_1$–C$_8$alkyl, C$_1$–C$_8$alkoxy and haloC$_1$–C$_8$alkoxy.

Certain compounds provided herein have one of the following formulas:

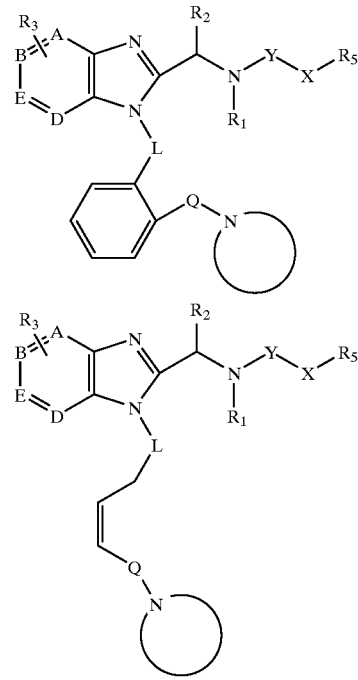

or a pharmaceutically acceptable salt thereof, wherein A, B, E, D, $R_1$, $R_2$, $R_3$, $R_5$, X, Y, L, and Q are as described above; and

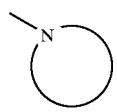

is ($C_5$–$C_7$)heterocycloalkyl, linked to Q via a nitrogen atom, and optionally substituted with from 1 to 3 substituents selected from hydroxy, halogen, amino, cyano, nitro, $C_1$–$C_6$alkyl, halo$C_1$–$C_8$alkyl, $C_1$–$C_6$alkoxy and halo$C_1$–$C_6$alkoxy.

Compounds provided herein preferably exhibit a $K_i$ of 500 nanomolar or less in an MCH receptor ligand binding assay, and a $K_i$ of greater than 1 micromolar in a human bradykinin $B_2$ receptor ligand binding assay.

Within further aspects, the present invention provides pharmaceutical compositions comprising a compound or modulator as described above in combination with a physiologically acceptable carrier or excipient. Within certain embodiments, a pharmaceutical composition provided herein may further comprise one or more additional active agents (i.e., drugs). Pharmaceutical compositions provided herein may be formulated, for example, as an injectible fluid, an aerosol, a cream, a gel, a pill, a capsule, a syrup or a transdermal patch.

The present invention further provides, within other aspects, methods for treating a disease or disorder associated with MCH receptor activation, comprising administering to a patient in need of such treatment an effective amount of a compound or modulator as described above. Such diseases and disorders include, for example, eating disorders (e.g., obesity and bulimia nervosa), sexual disorders, diabetes, heart disease and stroke. The compound or modulator may be administered orally, or via another means such as intranasally, intravenously or topically. Within certain embodiments, the patient is a human or a dog.

Within further aspects, compounds as described above are labeled with a detectable marker (e.g., radiolabeled or fluorescein-conjugated).

Methods are provided, within other aspects, for determining the presence or absence of MCH receptor in a sample, comprising the steps of: (a) contacting a sample with an agent comprising a compound as described above under conditions that permit binding of the agent to MCH receptor; and (b) detecting a level of agent bound to MCH receptor. Within certain embodiments, the agent is a radiolabeled compound, and the step of detection comprises the steps of: (i) separating unbound agent from bound agent; and (ii) detecting the presence or absence of bound agent in the sample.

The present invention further provides, within other aspects, methods for modulating binding of ligand to MCH receptor. Certain such methods are performed in vitro, and comprise contacting MCH receptor with a compound or modulator as described above under conditions and in an amount sufficient to detectably modulate MCH binding to MCH receptor. Other such methods may be performed in vivo, and comprise contacting cells expressing MCH receptor with a compound or modulator as described above in an amount sufficient to detectably modulate MCH binding to cells expressing a cloned MCH receptor in vitro. Modulation of MCH binding may be determined, for example, using a ligand binding assay as provided herein.

Methods are further provided for modulating binding of MCH to MCH receptor in a patient, comprising administering to a patient (i.e., a human or non-human animal) a compound or modulator as described above. Patients may include, for example, companion animals such as dogs.

Within certain embodiments of the above methods, the modulation is inhibition and/or the MCH receptor is a human MCH receptor.

Within further aspects, the present invention provides methods for modulating the signal-transducing activity of MCH receptor, comprising contacting an MCH receptor, either in vivo or in vitro, with a sufficient amount of an MCH receptor modulator, under conditions suitable for binding of MCH to MCH receptor.

Also provided by the present invention are packaged pharmaceutical preparations, comprising: (a) a pharmaceutical composition as described above in a container; and (b) instructions for using the composition to treat a patient suffering from a disease or disorder associated with MCH receptor activation. Such disorders include, for example eating disorders (e.g., obesity and bulimia nervosa), sexual disorders, diabetes, heart disease and stroke.

These and other aspects of the present invention will become apparent upon reference to the following detailed description.

DETAILED DESCRIPTION

As noted above, the present invention provides MCH receptor modulators comprising small molecule MCH receptor ligands that are substituted benzoimidazole analogues. Such modulators may be used in vitro or in vivo, to inhibit or enhance MCH binding to MCH receptors in a variety of contexts, as discussed in further detail below.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, n, $Ar_1$). Unless otherwise specified, each variable within such a formula is defined independently of other variable, and any variable that occurs more than one time in a formula is defined independently at each occurrence.

As used herein, a "1-benzyl-1H-benzoimidazol-2-yl-methyl analogue" or "benzoimidazole analogue" is a compound that satisfies the structure of Formula I. Such compounds include those in which $R_4$ is optionally substituted benzyl, as well as those in which $R_4$ is an optionally substituted alkene.

As used herein, the term "alkyl" refers to a straight chain, branched chain or cyclic saturated aliphatic hydrocarbon. An alkyl group may be bonded to an atom within a molecule of interest via any chemically suitable portion. Alkyl groups include groups having from 1 to 8 carbon atoms ($C_1$–$C_8$alkyl), from 1 to 6 carbon atoms ($C_1$–$C_6$alkyl) and from 1 to 4 carbon atoms ($C_1$–$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, cyclopropyl, cyclopropylmethyl, cyclopentyl, cyclopentylmethyl, cyclohexyl, cycloheptyl and norbornyl.

"$C_0$–$C_3$alkyl" refers to a bond or a $C_1$–$C_3$alkyl group.

Similarly, "alkenyl" refers to straight or branched chain alkene groups or cycloalkene groups. Within an alkenyl group, one or more unsaturated carbon-carbon double bonds are present. Alkenyl groups include $C_2$–$C_8$alkenyl, $C_2$–$C_6$alkenyl and $C_2$–$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have, one or more unsaturated carbon-carbon bonds, at least one of which is a triple bond. Alkynyl groups include $C_2$–$C_8$alkynyl, $C_2$–$C_6$alkynyl and $C_2$–$C_4$alkynyl groups, which have from 2 to 8, 2 to 2 or 2 to 4 carbon atoms, respectively.

By "$C_3$–$C_{10}$cycloalkyl" is meant alkyl groups having 3–10 carbon atoms forming a mono-, bi-, or polycyclic ring system, such as, for example, cyclopropyl, cyclopropylmethyl, cyclobutyl, cyclopentyl, cyclohexyl, cycloheptyl and norbornyl. "$C_4$–$C_8$cycloalkyl" and "$C_5$–$C_7$cycloalkyl" groups are those in which 4–8 or 5–7 carbon atoms form a single ring, respectively. Similarly, "$C_3$–$C_{10}$cycloalkenyl" refers to hydrocarbon groups having 3–10 carbon atoms forming a mono-, bi, or polycyclic ring system and containing one or more carbon-carbon double bonds which may occur at any stable point in the ring (e.g., cyclopentenyl, cyclohexenyl or cycloheptenyl). "($C_3$–$C_{10}$) cycloalkynyl" refers to hydrocarbon groups having 3–10 carbon atoms forming a mono-, bi, or polycyclic ring system and containing one or more carbon-carbon triple bonds which may occur at any stable point in the ring.

The term "(cycloalkyl)alkyl" or "($C_3$–$C_{10}$cycloalkyl) $C_1$–$C_8$alkyl" refers to a straight or branched alkyl substituent having 1 to 8 carbon atoms, that is further substituted with a mono-, bi, or polycyclic ring system having 3–10 carbon atoms (e.g., cyclopropylmethyl, cyclobutylmethyl, cyclopentylmethyl, cyclohexylmethyl and cycloheptylmethyl).

The term "hydroxy$C_1$–$C_8$alkyl" (or "hydroxy$C_1$–$C_6$alkyl") refers to aliphatic groups having from 1 to 8 (or 1 to 6) carbon atoms, and further comprising at least one hydroxyl group on the main carbon chain and/or on a side chain. Hydroxy$C_1$–$C_8$alkyl groups include, for example, 2-hydroxy-1,1-dimethyl-ethyl, 1-hydroxymethyl-2-methyl-propyl and 2-hydroxy-propyl.

By "alkoxy," as used herein, is meant an alkyl, alkenyl or alkynyl group as described above attached via an oxygen bridge. Alkoxy groups include $C_1$–$C_8$alkoxy, $C_1$–$C_6$alkoxy and $C_1$–$C_4$alkoxy groups, which have from 1 to 8, 1 to 6 or 1 to 4 carbon atoms, respectively. Alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy. Similarly, "$C_1$–$C_8$alkylthio" refers to an alkyl group of 1 to 8 carbon atoms attached via a sulfur bridge. "$C_3$–$C_{10}$ aryloxy" refers to aryl groups of 3 to 10 carbon atoms attached via an oxygen bridge (e.g., phenoxy).

The term "alkanoyl" refers to an acyl group in a linear, branched or cyclic arrangement (e.g., —(C=O)-alkyl). Alkanoyl groups include $C_2$–$C_8$alkanoyl, $C_2$–$C_6$alkanoyl and $C_2$–$C_4$alkanoyl groups, which have from 2 to 8, 2 to 6 or 2 to 4 carbon atoms, respectively.

An "alkanone" is a ketone group in which carbon atoms are in a linear, branched or cyclic alkyl arrangement. "$C_3$–$C_8$alkanone," "$C_3$–$C_6$alkanone" and "$C_3$–$C_4$alkanone" refer to an alkanone having from 3 to 8, 6 or 4 carbon atoms, respectively.

Similarly, "alkyl ether" refers to a linear or branched ether substituent linked via a carbon-carbon bond. Alkyl ether groups include $C_2$–$C_8$alkyl ether, $C_2$–$C_6$alkyl ether and $C_2$–$C_6$alkyl ether groups, which have 2 to 8, 6 or 4 carbon atoms, respectively.

The term "alkoxycarbonyl" refers to an alkoxy group linked via a carbonyl (e.g., a group having the general structure —C(=O)—O-alkyl). Alkoxycarbonyl groups include $C_2$–$C_8$, $C_2$–$C_6$ and $C_2$–$C_4$alkoxycarbonyl groups, which have from 2 to 8, 6 or 4 carbon atoms, respectively. $C_1$alkoxycarbonyl refers to —C(=O)OH, which is encompassed by the term "$C_1$–$C_8$alkoxycarbonyl."

"Alkanoyloxy," as used herein, refers to an alkanoyl group linked via an oxygen bridge (e.g., a group having the general structure —O—C(=O)-alkyl). Alkanoyloxy groups include $C_2$–$C_8$, $C_2$–$C_6$ and $C_2$–$C_4$alkanoyloxy groups, which have from 2 to 8, 6 or 4 carbon atoms, respectively. $C_1$alkanoyloxy refers to —O—C(=O)H, which is encompassed by the term "$C_1$–$C_8$alkanoyloxy."

The term "$C_1$–$C_8$carbonate" refers to an alkoxycarbonyl group linked via an oxygen bridge. In other words, a carbonate group has the general structure —O—C(=O)—O-alkyl. $C_1$–$C_6$carbonate groups are generally preferred, with $C_1$–$C_4$carbonate groups particularly preferred.

The term "$C_1$–$C_8$carbamate," as used herein, refers to a group having the general structure —N—C(=O)—O-alkyl. $C_1$–$C_6$carbamate groups are generally preferred, with $C_1$–$C_4$carbamate groups particularly preferred.

The term "halogen" includes fluorine, chlorine, bromine and iodine. A "haloalkyl" is a branched, straight-chain or cyclic alkyl group, substituted with 1 or more halogen atoms (e.g., "halo$C_1$–$C_8$alkyl" groups have from 1 to 8 carbon atoms; "halo$C_1$–$C_6$alkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Within certain compounds provided herein, not more than 5 or 3 haloalkyl groups are present. The term "haloalkoxy" refers to a haloalkyl group as defined above attached via an oxygen bridge. "Halo$C_1$–$C_8$alkoxy" groups have 1 to 8 carbon atoms.

A dash ("-") that is not between two letters or symbols is used to indicate a point of attachment for a substituent. For example, —CONH$_2$ is attached through the carbon atom.

A "heteroatom," as used herein, is oxygen, sulfur or nitrogen.

A "carbocycle" or "carbocyclic group" comprises at least one ring formed entirely by carbon-carbon bonds (referred to herein as a carbocyclic ring), and does not contain a heterocyclic ring. Unless otherwise specified, each carbocyclic ring within a carbocycle may be saturated, partially saturated or aromatic. A carbocycle generally has from 1 to 3 fused, pendant or spiro rings, carbocycles within certain embodiments have one ring or two fused rings. Typically, each ring contains from 3 to 8 ring members (i.e., $C_3$–$C_8$); $C_5$–$C_7$ rings are recited in certain embodiments. Carbocycles comprising fused, pendant or spiro rings typically contain from 9 to 14 ring members. Certain representative carbocycles are cycloalkyl (i.e., groups that comprise saturated and/or partially saturated rings, such as cyclopropyl, cyclobutyl, cyclopentyl, cyclohexyl, cycloheptyl, cyclooctyl, adamantyl, decahydro-naphthalenyl, octahydro-indenyl, and partially saturated variants of any of the foregoing, such as cyclohexenyl), as well as aromatic groups (i.e., groups that contain at least one aromatic carbocyclic ring, such as phenyl, benzyl, naphthyl, phenoxyl, benzoxyl, phenylethanonyl, fluorenyl, indanyl and 1,2,3,4-tetrahydro-naphthyl. Carbon atoms present within a carbocyclic ring may, of course, be further bonded to zero, one or two hydrogen atoms and/or any of a variety of ring substituents, such as hydroxy, halogen, cyano, nitro, $C_1$–$C_8$alkyl, $C_2$–$C_8$alkenyl, $C_2$–$C$alkynyl, $C_1$–$C_8$alkoxy, $C_2$–$C_8$alkyl ether, $C_3$–$C_8$alkanone $C_1$–$C_8$alkylthio, amino, mono- or di-($C_1$–$C_8$alkyl)amino, $C_3$–$C_7$cycloalkyl$C_0$–$C_4$alkyl, halo$C_1$–$C_8$alkyl, halo$C_1$–$C_8$alkoxy, amino$C_1$–$C_8$alkyl, hydroxy$C_1$–$C_8$alkyl, $C_2$–$C_8$alkanoyl, $C_2$–$C_8$alkoxycarbonyl, —COOH, —C(=O)NH$_2$, mono- or di-($C_1$–$C_8$alkyl) carboxamido, —S(O$_2$)NH$_2$ and/or mono- or di-($C_1$–$C_8$alkyl)sulfonamido. Within certain embodiments, $C_3$–$C_{10}$carbocycles that contain 1 carbocyclic ring or 2 fused carbocyclic rings (for a total of 3 to 10 ring members), optionally substituted, are preferred, with $C_5$–$C_{10}$carbocycles (i.e., groups with from 5 to 10 ring members and optional substitution(s)) particularly preferred.

A "heterocycle" or "heterocyclic group" has from 1 to 3 fused, pendant or spiro rings, at least one of which is a heterocyclic ring (i.e., one or more ring atoms is a heteroatom, with the remaining ring atoms being carbon). Typically, a heterocyclic ring comprises 1–4 heteroatoms; within certain embodiments each heterocyclic ring has 1 or 2 heteroatoms per ring. Each heterocyclic ring generally contains from 3 to 8 ring members (rings having from 5 to 7 ring members are recited in certain embodiments), and heterocycles comprising fused, pendant or spiro rings typically contain from 9 to 14 ring members. Heterocycles may be optionally substituted at nitrogen and/or carbon atoms with a variety of substituents, such as those described above for carbocycles. Unless otherwise specified, a heterocycle may be a heterocycloalkyl group (i.e., each ring is saturated or partially saturated) or a heteroaryl group (i.e., at least one ring within the group is aromatic). A heterocyclic group may generally be linked via any ring or substituent atom, provided that a stable compound results. N-linked heterocyclic groups are linked via a component nitrogen atom. A "heterocycle$C_0$–$C_8$alkyl" is a heterocyclic group linked via a direct bond or $C_1$–$C_8$alkyl group.

Heterocyclic groups include, for example, acridinyl, azepanyl, azocinyl, benzimidazolyl, benzimidazolinyl, benzisothiazolyl, benzisoxazolyl, benzofuranyl, benzothiofuranyl, benzothiophenyl, benzoxazolyl, benzothiazolyl, benzotriazolylcarbazolyl, benztetrazolyl, NH-carbazolyl, carbolinyl, chromanyl, chromenyl, cinnolinyl, decahydroquinolinyl, dihydrofuro[2,3-b] tetrahydrofuran, dihydroisoquinolinyl, dihydrotetrahydrofuranyl, 1,4-dioxa-8-aza-spiro[4.5]dec-8-yl, dithiazinyl, furanyl, furazanyl, imidazolinyl, imidazolidinyl, imidazolyl, indazolyl, indolenyl, indolinyl, indolizinyl, indolyl, isobenzofuranyl, isochromanyl, isoindazolyl, isoindolinyl, isoindolyl, isothiazolyl, isoxazolyl, isoquinolinyl, morpholinyl, naphthyridinyl, octahydroisoquinolinyl, oxadiazolyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, piperidinyl, piperidonyl, pteridinyl, purinyl, pyranyl, pyrazinyl, pyrazolidinyl, pyrazolinyl, pyrazolyl, pyridazinyl, pyridoimidazolyl, pyridooxazolyl, pyridothiazolyl, pyridyl, pyrimidyl, pyrrolidinyl, pyrrolidonyl, pyrrolinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienothiazolyl, thienooxazolyl, thienoimidazolyl, thienyl, thiophenyl, thiomorpholinyl and variants thereof in which the sulfur atom is oxidized, triazinyl, xanthenyl and any of the foregoing that are substituted with from 1 to 4 substituents as described herein. Preferred heterocyclic groups include, for example, benzo[b]thiophenyl and its substituted analogues, such as 3-chloro-benzo[b]thiophen-2-yl.

Certain aromatic heterocycles include 5- to 10-membered heteroaryl$C_0$–$C_8$alkyl groups (i.e., groups in which the heterocyclic group comprising at least one aromatic ring is linked via a direct bond or a $C_1$–$C_8$alkyl group). Such groups include, for example, the heteroaryl groups recited above, as well as groups in which any of the foregoing is linked via $C_1$–$C_8$alkyl, $C_1$–$C_6$alkyl or $C_1$–$C_4$alkyl. Representative aromatic heterocycles are azocinyl, pyridyl, pyrimidyl, imidazolyl, tetrazolyl and 3,4-dihydro-1H-isoquinolin-2-yl, as well as groups in which each of the foregoing is linked via $C_1$–$C_4$alkyl. Preferred heterocycloalkyls are 3- to 8-membered heterocycloalkyls such as piperidine and pyrrolidine.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution. When a substituent is keto (i.e., =O), then 2 hydrogens on the atom are replaced. Keto substituents are not present on aromatic moieties.

Groups that are "optionally substituted" are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$–$C_8$alkyl, $C_2$–$C_8$alkenyl, $C_2$–$C_8$alkynyl, $C_1$–$C_8$alkoxy, $C_2$–$C_8$alkyl ether, $C_3$–$C_8$alkanone, $C_1$–$C_8$alkylthio, amino, mono- or di-($C_1$–$C_8$alkyl)amino, halo$C_1$–$C_8$alkyl, halo$C_1$–$C_8$alkoxy, $C_2$–$C_8$alkanoyl, $C_2$–$C_8$alkanoyloxy, $C_2$–$C_8$alkoxycarbonyl, COOH, —CONH$_2$, mono- or di-($C_1$–$C_8$alkyl)carboxamido, —SO$_2$NH$_2$, and/or mono- or di-($C_1$–$C_8$alkyl)sulfonamido, as well as carbocyclic and heterocyclic groups. Certain optionally substituted groups are substituted with from 0 to 5 or from 0 to 3 independently selected substituents.

The term "MCH receptor" refers to a protein comprising any MCH receptor sequence (i.e., a cellular protein that detectably binds MCH and mediates a dose dependent release of intracellular calcium). Naturally-occurring mammalian (especially human and monkey) MCH type 1 or type 2 receptor sequences are generally preferred.

A "MCH receptor modulator," also referred to herein as a "modulator," is a compound that modulates (i.e., increases or decreases) MCH binding to one or more MCH receptors, as well as MCH receptor-mediated signal transduction. In other words, a modulator may be a MCH receptor agonist or antagonist. Modulators provided herein are generally substituted 1-benzyl-1H-benzoimidazol-2-yl-methyl analogues. A modulator binds with "high affinity" if the $K_i$ at an MCH receptor is less than 1 micromolar, preferably less than 100 nanomolar or 10 nanomolar. Preferred modulators bind to an MCH receptor with a $K_i$ that is less than 500 nanomolar (more preferably less than 100 nanomolar). Assays to evaluate an effect on MCH binding to MCH receptor, as well as MCH receptor-mediated signal transduction, may be performed using the binding and calcium mobilization assays provided herein within Examples 3 and 4, respectively. A modulator is considered an antagonist if it detectably inhibits MCH binding to MCH receptor and/or MCH receptor-mediated signal transduction (using, for example, the representative assay provided in Example 4). MCH receptor antagonists include neutral antagonists and inverse agonists.

A modulator binds "specifically" to MCH receptor if it binds to an MCH receptor (total binding minus nonspecific binding) with a $K_i$ that is 10-fold, preferably 100-fold, and more preferably 1000-fold, less than the $K_i$ measured for modulator binding to other G protein-coupled receptors (e.g., a bradykinin receptor). Preferred modulators bind to human bradykinin $B_2$ receptor with a $K_i$ that is greater than 1 micromolar (more preferably greater than 5 micromolar). An assay to evaluate binding to human bradykinin $B_2$ receptor is provided in Example 6 herein.

A "prodrug" is a compound that may not fully satisfy the structural requirements of the compounds provided herein, but is modified in vivo, following administration to a patient, to produce a substituted 1-benzyl-1H-benzoimidazol-2-yl-methyl analogue. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "patient" is any individual treated with a MCH receptor modulator as provided herein. Patients include humans, as well as other animals such as companion animals and livestock. Patients may be afflicted with a condition associated with undesirable MCH receptor activation, or may be free of such a condition (i.e., treatment may be prophylactic).

Melanin Concentrating Hormone Receptor Modulators

As noted above, the present invention provides melanin concentrating hormone (MCH) receptor modulators (i.e., compounds that detectably modulate MCH binding to MCH receptor and/or MCH-mediated signal transduction). Such modulators may be specific for a particular MCH receptor (e.g., type 1 or type 2), or may inhibit or enhance ligand binding to multiple MCH receptors. MCH receptor modulators may be used to modulate MCH binding to MCH receptors in vivo, especially in the treatment of metabolic, feeding and sexual disorders in humans, domesticated companion animals and livestock animals. Modulators may also be used within a variety of in vitro assays, such as assays for receptor activity, as probes for detection and localization of MCH receptors and as standards in assays of MCH binding and MCH-mediated signal transduction.

The MCH receptor modulators provided herein comprise active compound that are multi-aryl (i.e., have a plurality of unfused or fused aryl groups) and detectably modulate the binding of MCH to MCH receptor at nanomolar concentrations, preferably at subnanomolar concentrations. Active compounds are generally substituted 1-benzyl-1H-benzoimidazol-2-yl-methyl analogues, as defined above. Such compounds preferably bind specifically and with high affinity to an MCH receptor. Without wishing to be bound to any particular theory, it is believed that the interaction of the compounds provided herein with an MCH receptor results in the MCH receptor modulating activity of these compounds. Active compounds may include receptor agonists and antagonists.

The present invention is based, in part, on the discovery that small, amino acid-free molecules having the general Formula I (as well as pharmaceutically acceptable salts and prodrugs thereof) modulate MCH binding to MCH receptor.

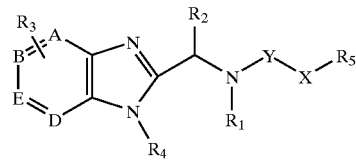

Formula I

Within Formula I, variables A, B, E, D, X, Y, $R_1$, $R_2$, $R_3$ and $R_5$ are generally as described above.

$R_4$ is a group that comprises (i) an aromatic ring or an alkenyl group, linked to (ii) a tertiary amine. Within certain embodiments, $R_4$ is L-$R_A$-Q-M, wherein L is $C_1$–$C_4$alkyl, preferably $C_1$–$C_3$alkyl, and more preferably —$CH_2$—; $R_A$ is phenyl, optionally substituted with from 1 to 3 substituents independently selected from hydroxy, halogen, amino, cyano, nitro, $C_1$–$C_6$alkyl and halo$C_1$–$C_6$alkyl; Q is a molecular unit selected from $C_0$–$C_3$alkyl, $C_2$–$C_3$alkenyl, $C_2$–$C_3$alkynyl, $C_1$–$C_3$alkoxy and $C_1$–$C_3$alkylthio, linked to $R_A$ at position 2; and M is tertiary amine. Within other embodiments, $R_4$ is L-$R_B$-Q-M, wherein L and M are as defined above; $R_B$ is $C_2$–$C_6$alkenyl, optionally substituted with from 1 to 3 substituents independently selected from hydroxy, halogen, amino, cyano, nitro, $C_1$–$C_6$alkyl and halo$C_1$–$C_6$alkyl; and Q is a molecular unit selected from $C_0$–$C_3$alkyl, $C_2$–$C_3$alkenyl, $C_2$–$C_3$alkynyl, $C_1$–$C_3$alkoxy and $C_1$–$C_3$alkylthio.

Preferred tertiary amines for use within $R_4$ have the formula:

wherein $R_6$ and $R_7$ each independently represent optionally substituted $C_1$–$C_8$alkyl, or wherein $R_6$ and $R_7$ jointly with the nitrogen atom to which they are bound form an optionally substituted 3 to 7 member heterocyclic ring. Substitutions for $R_6$ and $R_7$ occur at from 0 to 3 positions, with each substituent independently selected from hydroxy, halogen, amino, cyano, nitro, $C_1$–$C_8$alkyl, halo$C_1$–$C_8$alkyl, $C_1$–$C_8$alkoxy and halo$C_1$–$C_8$alkoxy. Particularly preferred tertiary amines are $C_5$–$C_7$cycloalkyl amino groups, especially those in which the tertiary amine is present within a 6-membered ring, such as piperidine, homopiperidine, morpholine and derivatives of the foregoing containing various substitutions (e.g., rings substituted with one or more small alkyl such as methyl, haloalkyl groups such as trifluoromethyl, alkoxy groups such as methoxy, haloalkoxy groups such as di- or trifluoromethoxy, and/or alkenes such as propene). Other suitable tertiary amines include, for example, pyridine, pyrrolidine and imidazole, and substituted derivatives thereof. Noncyclic tertiary amines in which the N is bonded to straight- or branched-chain lower alkyl groups (e.g., with 1 to 6 carbon atoms) are also suitable tertiary amines.

$R_1$, within Formula I, is generally a small nonaromatic group, optionally substituted with from 1 to 9, preferably from 1 to 3, substituents. Within certain embodiments, $R_1$ is hydrogen or a straight or branched chain lower alkyl or cycloalkyl with 1 to 6 carbon atoms (such as methyl, ethyl, isoamyl, isobutyl, n-butyl, n-propyl, cyclopropylmethyl or cyclopentylmethyl), a $C_2$–$C_6$alkyl ether, or mono- or di- ($C_1$–$C_6$alkyl)amino($C_1$–$C_6$alkyl). Alternatively, as noted above, $R_1$ is joined with $R_2$ to form an optionally substituted 5- to 7-membered heterocyclic ring that comprises the nitrogen to which $R_1$ is bound and the carbon to which $R_2$ is bound, optionally substituted. Preferred such rings are 5- or 6-membered.

$R_2$ of Formula I may also be a small, optionally substituted, typically nonaromatic group, as described above. Alternatively, $R_2$ is joined with $R_1$ to form a 5- to 7-membered heterocyclic ring as described above. Within certain embodiments, $R_2$ is hydrogen or a straight or branched chain lower alkyl or cycloalkyl with 1 to 6 carbon atoms (such as methyl, ethyl, isoamyl, isobutyl, n-butyl, n-propyl or cyclopropylmethyl.

$R_3$ represents up to four optional substituents of the ring comprising A, B, E and D. In other words, A, B, E and D may each be independently substituted with a group as described above. It will be apparent that only carbon atoms at A, B, E and D may be substituted; any position occupied by N, rather than CH, will not be substituted. Certain preferred $R_3$ substituents are trifluoromethyl and cyano; more preferably 0 or 1 of A, B, E and D is substituted.

Within certain embodiments, (i) A, B, E and D are each CH and/or (ii) Y is —(C=O)—.

$R_5$ represents a carbocyclic or heterocyclic group having from 1 to 3 fused or pendant rings, as described above. A ring within $R_5$ may be directly linked to X, or may be linked via a ring substituent. Certain $R_5$ groups are aromatic carbocyclic or heterocyclic groups having 1 or 2 fused or pendant rings, each ring containing from 5 to 6 ring members, wherein each group is optionally substituted as described above. Within certain embodiments, $R_5$ is a 3- to 10-member mono- or bicyclic aromatic group, (optionally substituted by from 1 to 3 substituents selected from halogen, $C_1$–$C_8$alkyl, halo$C_1$–$C_8$alkyl, $C_1$–$C_8$alkoxy, halo$C_1$–$C_8$alkoxy and $C_1$–$C_8$alkylthio), such as 3-chlorobenzo[b]thiophene, 2,3-difluorophenyl, 4-methylthiolphenyl, 2-ethoxyphenyl, 2-chloro-5-trifluoromethylphenyl, 1-naphthyl, 8-bromo-1-naphthyl, 3-fluoro-4-methoxyphenyl, 2-methyl-5-fluorophenyl, 4-chlorophenyl, 2,5-dichlorophenyl or 2-chlorothienyl. Certain preferred $R_5$ groups include:

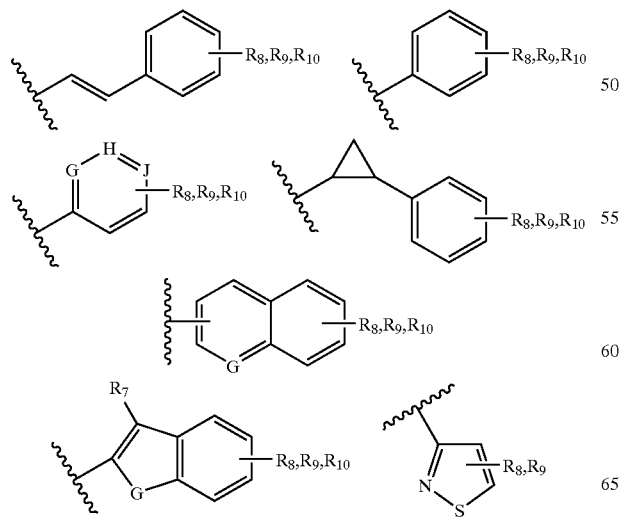

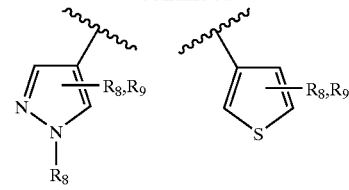

Within such $R_5$ groups, G, H and J are the same or different and represent CH or N, with the proviso that not more than one of G, H, and J represent N; and $R_8$, $R_9$ and $R_{10}$ are the same or different and represent hydrogen, $C_1$–$C_8$alkyl, halogen, nitro, phenyl, pyrrole, phenoxy, trifluoromethyl, trifluoromethoxy, cyano, $C_1$–$C_8$alkoxy, $C_1$–$C_8$alkylthio, hydroxy, amino or mono or dialkyl amino.

Within certain embodiments, compounds provided herein satisfy Formula II or Formula III (or are a pharmaceutically acceptable salt or prodrug of such a compound). Within Formulas II and III, A, B, E, D, $R_1$, $R_2$, $R_3$, $R_5$, X, Y, L, Q, $R_6$ and $R_7$ are as described above.

Formula II

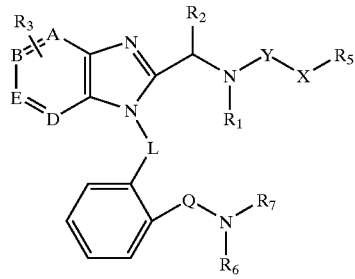

Formula III

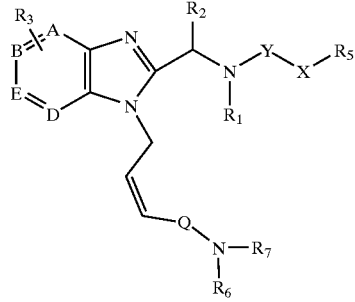

Certain such compounds satisfy Formula IIa or IIIa, or a pharmaceutically acceptable salt or prodrug thereof, wherein A, B, E, D, $R_1$, $R_2$, $R_3$, $R_5$, X, Y, L and Q are as described above.

Formula IIa

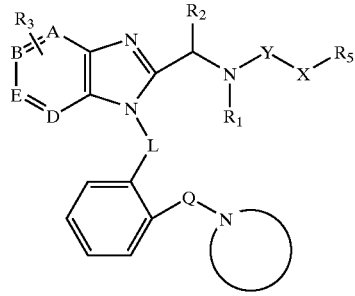

-continued

Formula IIIa

Within Formulas IIa and IIIa, is a nitrogen-containing $C_5$–$C_7$heterocycloalkyl, linked to Q via a ring nitrogen atom, and optionally substituted with from 1 to 3 substituents selected from hydroxy, halogen, amino, cyano, nitro, $C_1$–$C_6$alkyl, halo$C_1$–$C_8$alkyl, $C_1$–$C_6$alkoxy and halo$C_1$–$C_6$alkoxy. The nitrogen-containing $C_5$–$C_7$heterocycloalkyl is preferably piperidinyl, pyrrolidinyl, morpholinyl, hexamethyleneiminyl or piperazinyl, optionally substituted with from 1 to 3 substituents selected from hydroxy, halogen, amino, cyano, nitro, $C_1$–$C_8$alkyl and halo$C_1$–$C_8$alkyl, and Q is preferably —$CH_2$—. Within certain embodiments, Q is —$CH_2$—, L is —$CH_2$— and the nitrogen-containing $C_5$–$C_7$) heterocycloalkyl is piperidinyl.

Certain specific MCH receptor modulators provided herein are recited in Examples 1 and 2. It will be apparent that the specific compound recited therein are representative only, and are not intended to limit the scope of the present invention. Further, as noted above, all compounds of the present invention may be present as a hydrate, free base or a pharmaceutically acceptable acid addition salt.

Substituted benzoimidazole analogues provided herein detectably alter (modulate) MCH binding to MCHR1 and/or MCHR2 receptor, as determined using a standard in vitro MCH receptor ligand binding assay and/or calcium mobilization assay. References herein to a "MCH receptor ligand binding assay" are intended to refer to a standard in vitro receptor binding assay as provided in Example 3. Briefly, a competition assay may be performed in which an MCH receptor preparation is incubated with labeled (e.g., $^{125}$I) MCH and unlabeled test compound. Within the assays provided herein, the MCH receptor used is preferably a mammalian MCHR1 or MCHR2 receptor, more preferably a human or monkey MCHR1 or MCHR2 receptor. The MCH receptor preparation may be, for example, a membrane preparation from HEK293 cells that recombinantly express a monkey MCH receptor (such as the MCHR1 sequence provided in SEQ ID NOs:1 and 2), human MCHR1 receptor (GenBank Accession No. AB063 174), or human MCHR1/human beta-2-adrenergic receptor.

Incubation with a compound that detectably modulates MCH binding to MCH receptor will result in a decrease or increase in the amount of label bound to the MCH receptor preparation, relative to the amount of label bound in the absence of the compound. Preferably, such a compound will exhibit a $K_i$ at an MCH receptor of less than 1 micromolar, more preferably less than 500 nM, 100 nM, 20 nM or 10 nM, within a MCH receptor ligand binding assay performed as described in Example 3. Generally preferred compounds are MCH receptor antagonists, and exhibit $EC_{50}$ values of about 4 micromolar or less, more preferably 1 micromolar or less, still more preferably about 100 nanomolar or less, 10 nanomolar or less or 1 nanomolar or less within a standard in vitro MCH receptor mediated calcium mobilization assay, as provided in Example 4.

Within certain embodiments, modulators provided herein do not substantially modulate ligand binding to human bradykinin $B_2$ receptor. In other words, such modulators bind to MCH receptor with a Ki that is at least 10-fold, preferably 100-fold and more preferably 1000-fold less than the Ki measured for modulator binding to human bradykinin $B_2$ receptor. In general, such modulators bind to MCH receptor with a Ki that is less than 500 nanomolar, preferably less than 100 nanomolar and more preferably less than 10 nanomolar (as determined using an assay provided in Example 3 herein); and such modulators bind to human bradykinin $B_2$ receptor with a Ki that is greater than 1 micromolar, preferably greater than 2, 5 or 10 micromolar (as determined using an assay provided in Example 6 herein). Binding to human bradykinin B2 receptor may be assessed using any standard in vitro bradykinin $B_2$ receptor ligand binding assay. References herein to a "bradykinin $B_2$ receptor ligand binding assay" are intended to refer to the standard in vitro receptor binding assay provided in Example 6. Briefly, a competition assay may be performed in which a human bradykinin $B_2$ receptor preparation is incubated with labeled (e.g., $^3$H) bradykinin and unlabeled test compound. The receptor may be recombinantly expressed or naturally expressed. The bradykinin $B_2$ receptor preparation may be, for example, a membrane preparation from baculovirus-infected Sf9 cells expressing recombinant human bradykinin $B_2$ receptor (such as the human bradykinin $B_2$ receptor sequence described by Menke et al. (1994) J. Biol. Chem. 21583–86).

It has been found that the nature of the $R_5$ substituent is particularly important for binding to human bradykinin $B_2$ receptor. In particular, certain compounds in which Y is the group —(C=O)—, X is a bond, and $R_5$ is phenyl substituted with a halogen and two alkoxy groups can be especially active at the bradykinin $B_2$ receptor. Accordingly, particularly preferred compounds do not comprise such an $R_5$ group.

In addition, or alternatively, preferred compounds of the present invention do not substantially interact with dopamine receptors, particularly human dopamine D2 and D4 receptors. Dopamine receptor binding assays may be performed using standard methods, such as the assay described in Example 5. Preferably, compounds exhibit $K_i$ values greater than 1 micromolar within such an assay.

If desired, compounds provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred compound is nontoxic when a therapeutically effective amount is administered to a subject), side effects (a preferred compound produces side effects comparable to placebo when a therapeutically effective amount of the compound is administered to a subject), serum protein binding and in vitro and in vivo half-life (a preferred compound exhibits an in vitro half-life that is equal to an in vivo half-life allowing for Q.I.D dosing, preferably T.I.D. dosing, more preferably B.I.D. dosing, and most preferably once-a-day dosing). In addition, differential penetration of the blood brain barrier may be desirable for compounds used to treat CNS disorders, while low brain levels of compounds used to treat peripheral disorders may be preferred (i.e., such doses do not provide brain (e.g., CSF) levels of the compound sufficient to significantly modulate MCH receptor activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Such assays are described in a review by Oravcova, et al. (Journal of Chromatography B (1996) volume 677, pages 1–27). Compound half-life is inversely proportional to the frequency of dosage of a compound. In vitro half-lives of compounds may be predicted from assays of microsomal half-life as described within Example 8, herein.

Toxicity and side effects may be assessed using any standard method. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). Toxicity may be also evaluated using the assay detecting an effect on cellular ATP production provided in Example 7. Other assays that may be used include bacterial reverse mutation assays, such as an Ames test, as well as standard teratogenicity and tumorogenicity assays. Preferably, administration of compounds provided herein at certain doses (i.e., doses yielding therapeutically effective in vivo concentrations or preferably doses of 0.01, 0.05, 0.1, 0.5, 1, 5, 10, 40, or 50 mg/kg administered parenterally or orally) does not result in prolongation of heart QT intervals (i.e., as determined by electrocardiography in guinea pigs, minipigs or dogs). When administered daily for five or preferably ten days, such doses also do not cause liver enlargement resulting in an increase of liver to body weight ratio of more than 100%, preferably not more than 75% and more preferably not more than 50% over matched controls in laboratory rodents (e.g., mice or rats). Such doses also preferably do not cause liver enlargement resulting in an increase of liver to body weight ratio of more than 50%, preferably not more than 25%, and more preferably not more than 10% over matched untreated controls in dogs or other non-rodent mammals.

Preferred compounds also do not promote substantial release of liver enzymes (e.g., ALT, LDH, or AST) from hepatocytes in vivo. Preferably the above doses do not elevate serum levels of such enzymes by more than 100%, preferably not by more than 75% and more preferably not by more than 50% over matched untreated controls in vivo in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause detectable release of any of such liver enzymes from hepatocytes in vitro into culture medium above baseline levels seen in media from untreated cells.

Preferred compounds further do not exhibit significant activity as sodium ion channel blockers, exhibiting less than 15 percent inhibition, and more preferably less than 10 percent inhibition, of sodium channel specific ligand (e.g., batrachotoxin, tetrodotoxin or saxitoxin) binding when present at a concentration of 4 $\mu$M or less. Assays for sodium channel specific ligand binding are well known in the art. In addition, preferred compounds do not exhibit significant androgen antagonist activity (e.g., in vivo, in a Hershberger assay, or in vitro, in an assay such as that described by Nellemann et al. (2001) Toxicology 163(1):29–38). Preferred compounds exhibit less than a 15% inhibition, more preferably less than a 10% inhibition, and most preferably less than 5% inhibition of androgen receptor activation in the in vitro assay when present at concentrations of 4 $\mu$M or less. By significant activity is meant results varying from control at the p<0.1 level or more preferably at the p<0.05 level of significance as measured using a standard parametric assay of statistical significance such as a student's T test.

For detection purposes, as discussed in more detail below, compounds provided herein may be isotopically-labeled or radiolabeled. Accordingly, compounds recited in Formula I may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^{2}$H) can afford certain therapeutic advantages resulting from greater metabolic stability, for example increased in vivo half-life or reduced dosage requirements and, hence, may be preferred in some circumstances.

Preparation of MCH Receptor Modulators

Substituted benzoimidazole analogues may generally be prepared using standard synthetic methods. In general, starting materials are commercially available from suppliers such as Sigma-Aldrich Corp. (St. Louis, Mo.). For example, a synthetic route similar to that shown in Scheme I may be used. Numbers used within the following description refer only to the numbers in Scheme I. As shown in Scheme I, compound of general structure 1 can be prepared by treatment of 2-cyanobenzyl bromide with secondary amine of general structure 4 followed by reduction to afford compound of general structure 2. Treatment of 2 with a compound of general structure 5 followed by reduction and ring closure can afford a compound of general structure 1. Compound 1 can be treated with amines of general structure 7 and subsequent acylation with acid chlorides or carboxylic acids of general structure 8 to afford compounds of Formula II, in which $R_4$ is a substituted benzyl group. Those having skill in the art will recognize that the starting materials may be varied and additional steps employed to produce other compounds encompassed by the present invention.

Scheme I

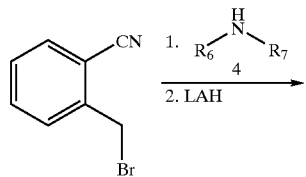

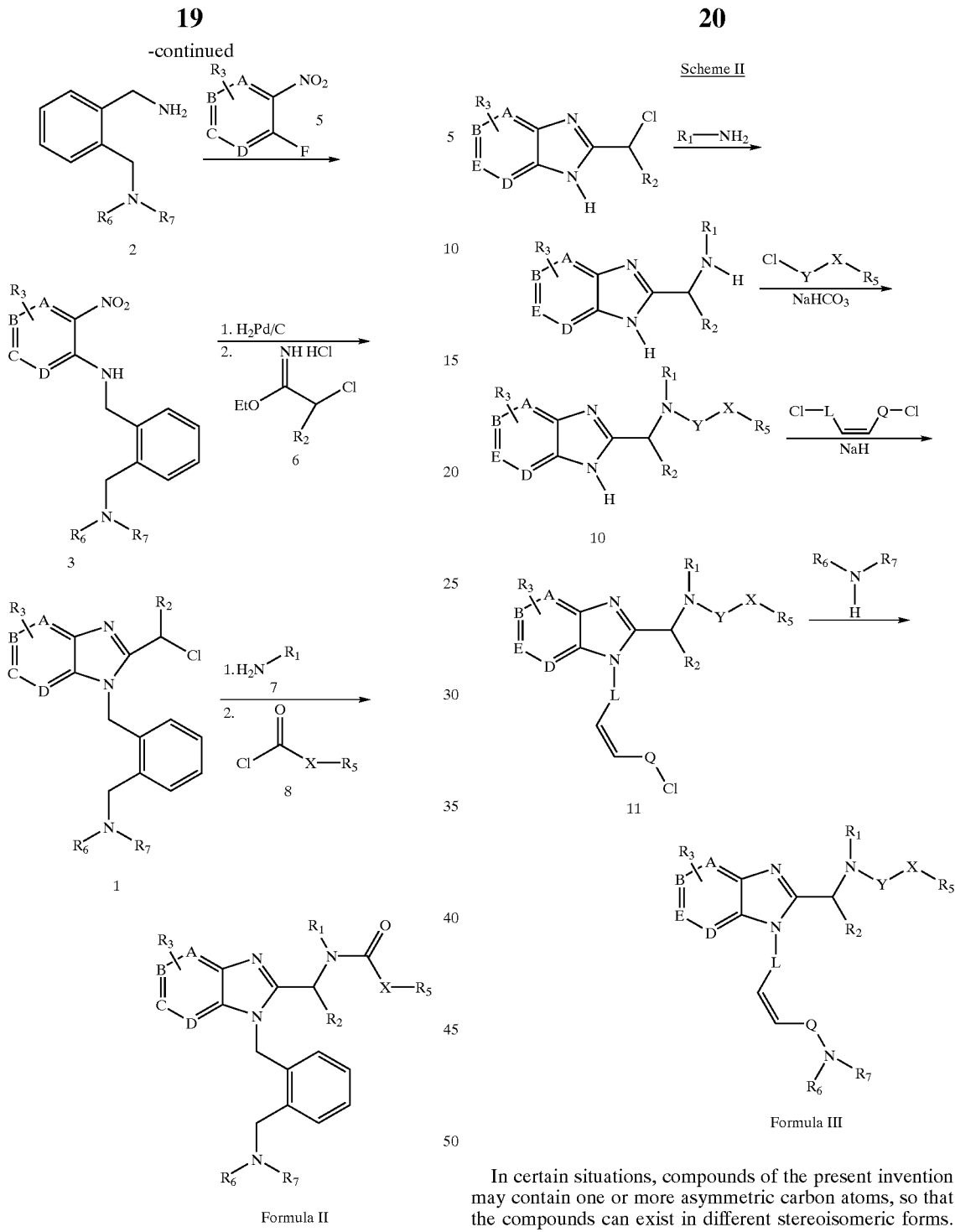

Formula II

Scheme II

Formula III

The synthetic route shown in Scheme II can be used to prepare compounds of Formula III. Numbers referred to in the following discussion refer to those in Scheme II. As shown in Scheme II, treatment of a chloromethylbenzimidazole derivative with an amine yields the aminobenzimidazole derivative. This derivative is treated with a benzoyl-, thiobenzoyl-, sulfenyl- or sulfanoyl chloride (i.e., Y is —(C=O)—, —(C=S)—, —(S=O)— or —(SO$_2$)—), to yield a compound of general structure 10. The compound of structure 10 is then reacted with sodium hydride and a cis-dichloroalkene to yield a compound of general structure 11. Reaction with a secondary amine results in a compound of Formula III.

In certain situations, compounds of the present invention may contain one or more asymmetric carbon atoms, so that the compounds can exist in different stereoisomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Prodrugs of the compounds provided herein may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$), or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising a MCH receptor modulator as described herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

If desired, other active ingredients may also be included. For example, compositions intended for the treatment of eating disorders, particularly obesity and bulimia nervosa, may further comprise leptin, a leptin receptor agonist, a melanocortin receptor 4 ($MC_4$), sibutramine, dexenfluramine, a growth hormone secretagogue, a beta-3 agonist, a 5HT-2 agonist, an orexin antagonist, a neuropeptide $Y_1$ or $Y_5$ antagonist, a galanin antagonist, a CCK agonist, a GLP-1 agonist and/or a corticotropin-releasing hormone agonist.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral delivery to humans or other animals (e.g., companion animals such as dogs) are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally present within a pharmaceutical composition in a therapeutically effective amount. A therapeutically effective amount is an amount that results in a discernible patient benefit, such as increased healing of a disease or disorder associated with pathogenic MCH receptor, as described herein. A preferred amount will result in a concentration in a body fluid (e.g., blood, plasma, serum, CSF, synovial fluid, lymph, cellular interstitial fluid, tears or urine) that is sufficient to sufficient to inhibit the binding of MCH to MCH receptor in vitro. Compositions providing dosage levels ranging from about 0.1 mg to about 140 mg per kilogram of body weight per day are generally preferred (about 0.5 mg to about 7 g per human patient per day).

The amount of active ingredient that may be combined with the carrier materials to produce a single dosage form will vary depending, for example, upon the patient being treated and the particular mode of administration. Dosage unit forms will generally contain between from about 1 mg to about 500 mg of an active ingredient. Optimal dosages may be established using routine testing, and procedures that are well known in the art.

Pharmaceutical compositions may be packaged for treating disorders responsive to melanin concentrating hormone receptor modulation (e.g., treatment of metabolic disorders such as diabetes, heart disease, stroke, eating disorders such as obesity or bulimia, or sexual disorders such as anorgasmic or psychogenic impotence). Packaged pharmaceutical compositions may include a container holding a therapeutically effective amount of at least one MCH receptor modulator as described herein and instructions (e.g., labeling) indicating that the contained composition is to be used for treating a disorder responsive to MCH receptor modulation in the patient.

Methods of Use

MCH receptor modulators provided herein may be used as agonists or (preferably) antagonists of MCH receptor(s) in a variety of contexts, both in vitro and in vivo. Within certain aspects, MCH receptor antagonists may be used to inhibit the binding of MCH receptor ligand (such as MCH) to MCH receptor in vitro or in vivo. In general, such methods comprise contacting a MCH receptor with a sufficient amount of one or more MCH receptor modulators provided herein, in the presence of MCH receptor ligand in aqueous solution and under conditions otherwise suitable for binding of the ligand to MCH receptor. The MCH receptor may be present in solution or suspension (e.g., in an isolated membrane preparation), in a cultured or isolated cell preparation or within a patient. Preferably, the MCH receptor is a MCHR1 receptor present in the hypothalamus. In general, the amount of MCH receptor antagonist contacted with the receptor should be sufficient to yield a concentration in the aqueous solution sufficient to inhibit MCH receptor ligand binding to MCH receptor in vitro within, for example, a binding assay as described in Example 3 and/or a calcium mobilization assay as described in Example 4.

Also provided herein are methods for modulating, preferably inhibiting, the signal-transducing activity of a MCH receptor. Such modulation may be achieved by contacting a MCH receptor (either in vitro or in vivo in a human or animal) with an effective amount of one or more MCH receptor modulators under conditions suitable for binding of the modulator(s) to the receptor. Preferably, within such methods, signal-transducing activity is inhibited by the modulator. The receptor may be present in solution or suspension, in a cultured or isolated cell preparation or within a patient. Modulation of signal tranducing activity may be assessed by detecting an effect on calcium ion conductance (also referred to as calcium mobilization or flux). In general, an effective amount of MCH receptor modulator(s) is an amount sufficient to yield a concentration (in an aqueous solution that is in contact with the receptor) that is sufficient to modulate MCH receptor signal transducing activity in vitro within a calcium mobilization assay as described in Example 4. MCH receptor modulator(s) are preferably administered to a patient (e.g., a human.) orally or topically, and are present within at least one body fluid of the patient while modulating MCH receptor signal-transducing activity.

The present invention further provides methods for treating conditions responsive to MCH receptor modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to MCH receptor modulation" if it is characterized by inappropriate activity of a MCH receptor (i.e., is associated with pathogenic MCH receptor activity), regardless of the amount of MCH receptor ligand present locally, and/or if modulation of MCH receptor activity results in alleviation of the condition or a symptom thereof. Such conditions include, for example, metabolic disorders (such as diabetes), heart disease, stroke, eating disorders (such as obesity and bulimia nervosa), or sexual disorders such as anorgasmic or psychogenic impotence. These conditions may be diagnosed and monitored using criteria that have been established in the art. Patients may include humans, domesticated companion animals (pets, such as dogs) and livestock animals, with dosages and treatment regimes as described above.

Treatment regimens may vary depending on the compound used and the particular condition to be treated. However, for treatment of most disorders, a dosage regimen (frequency of administration) of 4 times daily or less is preferred. For the treatment of eating disorders, including obesity, a dosage regimen of 1 or 2 times daily is particularly preferred. For the treatment of impotence a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose that is sufficient to provide effective therapy is preferred. Patients may generally be monitored for therapeutic effectiveness using medical or veterinary criteria suitable for the condition being treated or prevented, which will be familiar to those of ordinary skill in the art.

Within separate aspects, the present invention provides a variety of in vitro uses for the compounds provided herein. For example, such compounds may be used as probes for the detection and localization of MCH receptors, in samples such as tissue sections, as positive controls in assays for receptor activity, as standards and reagents for determining the ability of a candidate agent to bind to MCH receptor, or as radiotracers for positron emission tomography (PET) imaging or for single photon emission computerized tomography (SPECT). Such assays can be used to characterize MCH receptors in living subjects.

Within methods for determining the presence or absence of MCH receptor in a sample, a sample may be incubated with a compound as provided herein under conditions that permit binding of the compound to MCH receptor. The amount of compound bound to MCH receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of MCH receptor in the sample. Detection assays, including receptor autoradiography (receptor mapping) of MCH receptors in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use in immobilizing and thereby isolating MCH-expressing cells for screens, assays and growth in culture. Modulators may also be used to facilitate cell identification and sorting in vitro, permitting the selection of cells expressing a MCH receptor. Preferably, the modulator(s) for use in such methods are labeled as described herein. Within one preferred embodiment, a modulator linked to a fluorescent marker, such as fluorescein, is contacted with the cells, which are then analyzed (or isolated) by fluorescence activated cell sorting (FACS).

The following Examples are offered by way of illustration and not by way of limitation. Unless otherwise specified all reagents and solvent are of standard commercial grade and are used without further purification.

EXAMPLES

Example 1

Preparation of Representative MCH Receptor Modulators

This Example illustrates the preparation of representative MCH receptor modulators of Formulas II and III.

A. N-Butyl-2,3-difluoro-N-[1-(2-piperidin-1-ylmethyl-benzyl)-1H-benzoimidazol-2-ylmethyl]-benzamide Scheme III:

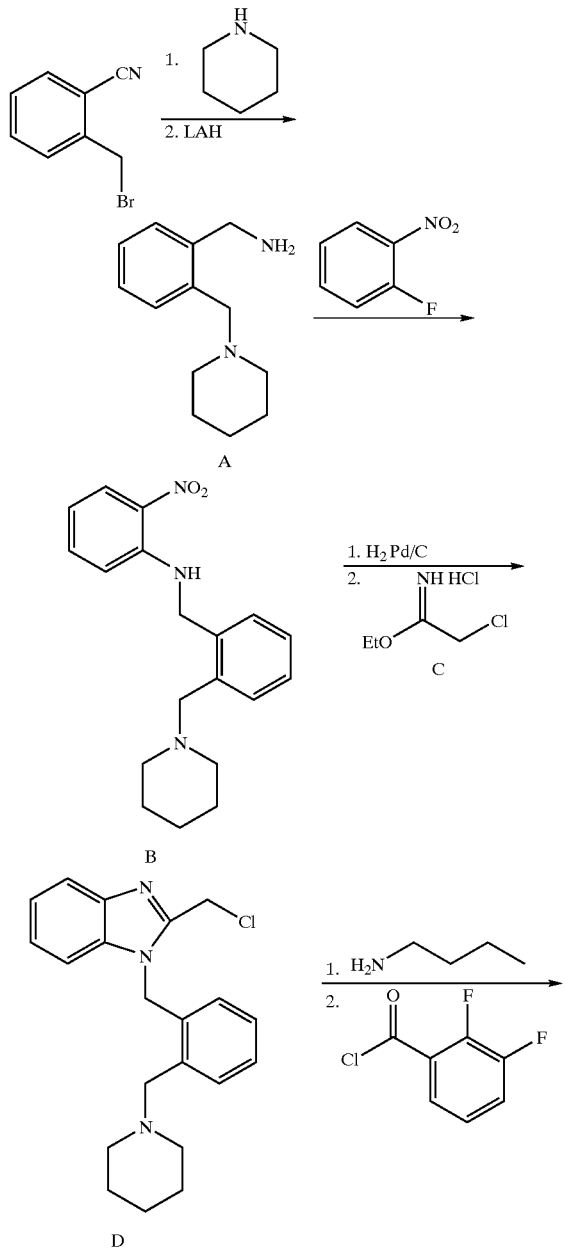

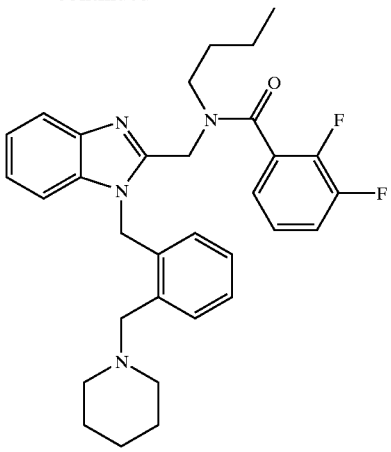

A solution of 35 g (0.18 mole) of cyanobromotoluene and 16.18 g (0.19 mole) of piperidine in 300 mL of anhydrous DMF was treated with 73 g (0.5 mole) of $K_2CO_3$ at 50° C. for 2 hr. The reaction mixture was filtered through a plug of Celite, washed with 400 mL of ethyl acetate, and the filtrate was partitioned between ethyl acetate and ½ saturated brine. The organic layer was dried over anhydrous $Na_2SO_4$ and concentrated in vacuo, yielding 36 g (0.18 mole) 100% of 2-Piperidin-1-ylmethyl-benzonitrile. $^1$H NMR (300 MHz, $CDCl_3$) 7.6 (m, 3H), 7.24 (m, 1H), 3.6 (s, 2H), 2.4 (m, 4H), 1.5 (m, 6H).

A solution of 5 g (0.025 mole) of 2-Piperidin-1-ylmethyl-benzonitrile in 100 mL of anhydrous THF was treated with 0.95 g (0.025 mole) of LAH at 0° C. for 2 hr. An excess of $Na_2CO_3 \cdot 10H_2O$ was added and the resulting mixture was filtered through a plug of Celite and washed with 200 mL of anhydrous THF. The solution was concentrated to yield 4.4 g (0.021 mole) 84% of compound A. $^1$H NMR (300 MHz, $CDCl_3$) 7.2 (m, 4H), 3.8 (s, 2H), 3.4 (s, 2H) 2.4 (m, 4H), 1.4 (m, 6H).

A solution of 4.4 g (0.021 mole) of compound A was treated with 2.2 mL (0.021 mole) of fluoronitro benzene in 100 mL of anhydrous DMF with 8.9 g (0.06 mole) of $K_2CO_3$ at room temperature overnight. The resulting solution was filtered through a plug of Celite and washed with 400 mL of ethyl acetate. The filtrate was partitioned between ethyl acetate and ½ saturated brine and dried over anhydrous $Na_2SO_4$. The resulting oil was flash chromatographed on $SiO_2$ with 50% ethyl acetate/hexanes to yield 6.0 g (0.018 mole) 88% of compound B. $^1$H NMR (300 MHz, $CDCl_3$) 8.5 (s, NH), 8.2 (m, 1H), 7.23 (m, 5H), 6.9 (m, 1H), 6.6 (m, 1H), 4.8 (s, 2H), 3.41 (s, 2H) 2.4 (s, 4H), 1.4 (m, 6H).

A solution of 6.0 g (0.018 mole) of compound B, 0.6 g 10% Pd/C in 100 mL 1:1 ethanol ethyl acetate is treated at room temperature with 40 psi of hydrogen for 2 hr. The resulting solution was filtered through a plug of Celite and washed with 100 mL of ethanol. The resulting solution was concentrated and the residue is taken up in 200 mL of anhydrous ethanol and treated with 6.7 g (0.042 mole) of imidate C at room temperature for 2 hr. The resulting solution was concentrated and partitioned between ethyl acetate and sat. $NaHCO_3$. The organic layer was dried over anhydrous $Na_2SO_4$ and concentrated. The resulting oil was chromatographed on $SiO_2$ with 50% ethyl acetate/hexanes and the HBr salt made to yield 5.6 g (0.012 mole 71%) of compound D. LCMS MF=C21H24N3Cl MW=353.9 found 354 ($M^+$).

A solution of 0.9 g (1.7 mmole) of compound D was treated with 10 mL of butyl amine in 50 mL of acetonitrile at room temperature for 2 hr. The resulting solution was concentrated and partitioned between ethyl acetate and 1N NaOH. The organic layer was dried over anhydrous $Na_2SO_4$ and concentrated to yield 0.55 g of Butyl-[1-(2-piperidin-1-ylmethyl-benzyl)-1H-benzoimidazol-2-ylmethyl]-amine. $^1$H NMR (300 MHz, $CDCl_3$) 7.8 (d, 1H), 7.2 (m, 5H), 7.05 (d, 1H), 6.4 (d, 1H), 5.8 (s, 2H), 4.0 (s, 2H), 3.6 (s, 2H), 2.6 (t, 2H), 1.2–1.6 (m, 14H), 0.8 (t, 3H). A quantity of 0.1 mL of a 0.2 M solution of Butyl-[1-(2-piperidin-1-ylmethyl-benzyl)-1H-benzoimidazol-2-ylmethyl]-amine in toluene is treated with 0.15 mL of a 0.2 M solution of 2,3-Difluorobenzoyl chloride in dichloroethane at room temperature for 1 hr. The resulting mixture was chromatographed on $SiO_2$ with ethyl acetate to yield 9 mg of N-Butyl-2,3-difluoro-N-[1-(2-piperidin-1-ylmethyl-benzyl)-1H-benzoimidazol-2-ylmethyl]-benzamide. LCMS MF=$C_{32}H_{36}F_2N_4O$ MW=530.6 found 531.

B. N-Butyl-2,3-difluoro-N-[1-(4-piperidin-1-yl-but-2-Enyl)-1H-benzoimidazol-2-ylmethyl]-benzamide

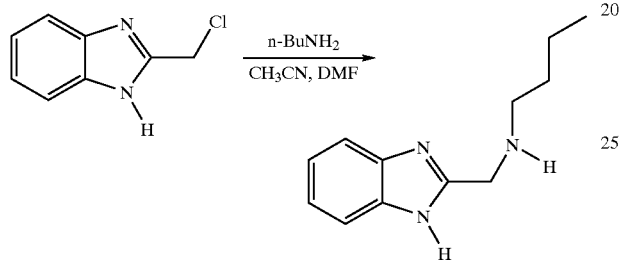

Butylamine (30 mL, 300 mmol) was dissolved in 150 mL of acetonitrile at room temperature. 2-Chloromethylbenzimidazole (5 g, 30 mmol) dissolved in 50 mL dimethylformamide was added dropwise. After stirring 3 hours at room temperature, the solvent was removed in vacuo. The residue was dissolved in 100 mL ethyl acetate and washed 2×100 mL $H_2O$ followed by 1×100 mL brine. The organic layer was dried over $MgSO_4$, filtered, and then concentrated. The residue was purified by silica gel chromatography eluting first with ethyl acetate then with 10/2/1 ethyl acetate/methanol/triethylamine to yield 2.6 g 2-butylaminomethylbenzimidazole.

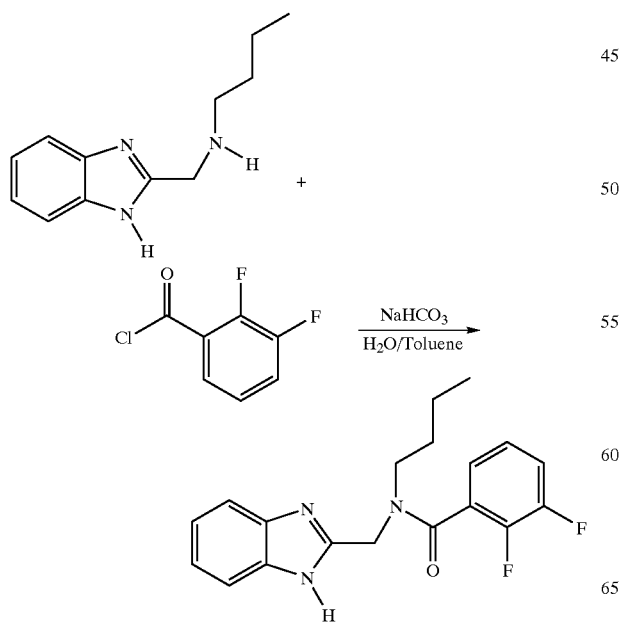

2-butylaminomethylbenzimidazole (2.6 g, 13 mmol) was dissolved in 30 mL toluene. Saturated $NaHCO_3$ solution (30 mL) was added followed by 2,3-difluorobenzoyl chloride (1.3 mL, 10 mmol). The reaction mixture was stirred at room temperature for 3 hours. The reaction mixture was diluted with 100 mL ethyl acetate then washed 1×100 mL 1N NaOH followed by 1×100 mL $H_2O$. The organic phase was dried over $MgSO_4$, filtered, and then concentrated. The residue was purified by flash chromatography eluting with 1/1 ethyl acetate/hexane followed by ethyl acetate to afford 2.0 g N-butyl-N-(1H-benzoimidazol-2-ylmethyl)-2,3-difluorobenzamide.

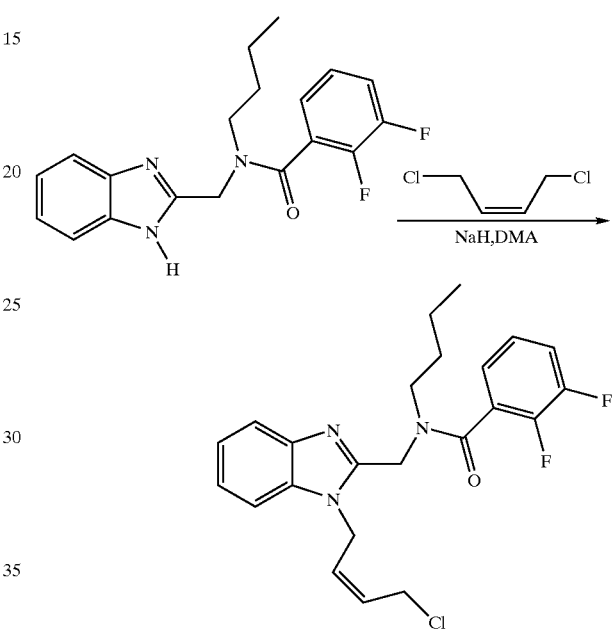

N-butyl-N-(1H-benzoimidazol-2-ylmethyl)-2,3-difluorobenzamide (226 mg, 0.66 mmol) was dissolved in 3 mL dimethylacetamide at room temperature. Sodium hydride (29 mg, 0.72 mmol, 60% oil dispersion) was added and the reaction mixture stirred 5 minutes. Cis-1,4-Dichloro-2-butene was added and the reaction mixture stirred 90 minutes. The reaction mixture was diluted with 10 mL ethyl acetate, placed in a separatory funnel and washed 1×10 mL $H_2O$ then 1×10 mL brine. The organic phase was dried over $MgSO_4$, filtered, concentrated, then purified by flash chromatography eluting with 1/1 ethyl acetate/hexane to afford 206 mg 2,3-difluoro-N-butyl-N-[(4-chlorobut-2-enyl)-1H-benzoimidazol-2-ylmethyl]-benzamide.

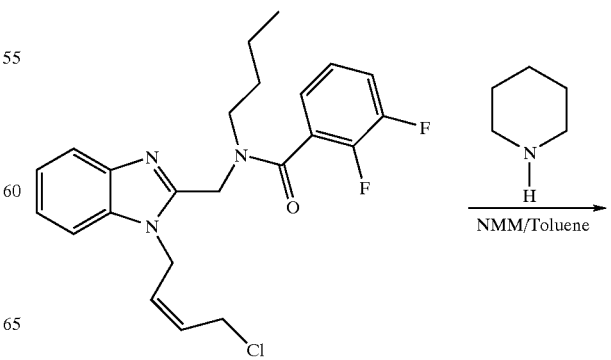

-continued

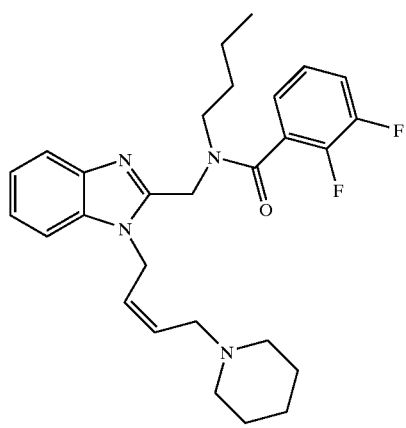

2,3-Difluoro-N-butyl-N-[(4-chlorobut-2-enyl)-1H-benzoimidazol-2-ylmethyl)-benzamide (26 mg, 0.06 mmol) was dissolved in 0.3 mL toluene. Piperidine (10 µL, 0.1 mmol) dissolved in 0.5 mL 95/5 toluene/4-methylmorpholine was added and the reaction mixture was heated at 90° C. for 15 hours. The reaction mixture was cooled to room temperature and deposited on a 1 g silica SPE column. The column was washed with 4 mL ethyl acetate to remove impurities followed by 4 mL 10/2/1 ethyl acetate/methanol/triethylamine to elute the product to afford 24 mg N-butyl-2,3-difluoro-N-[1-(4-piperidin-1-yl-but-2-enyl)-1H-benzoimidazol-2-ylmethyl]-benzamide.

Example 2

Preparation of Additional Representative MCH Receptor Modulators

By readily apparent variation of the above methods, the following additional representative compounds were prepared.

| | Compound | Name |
|---|---|---|
| 1. | | (2,3-Difluoro-phenyl)-{2-[1-(2-piperidin-1-ylmethyl-benzyl)-1H-benzoimidazol-2-yl]-pyrrolidin-1-yl}-methanone |
| 2. | | (2,3-Difluoro-phenyl)-{2-[1-(2-piperidin-1-ylmethyl-benzyl)-1H-benzoimidazol-2-yl]-piperidin-1-yl}-methanone |

| | Compound | Name |
|---|---|---|
| 3. | | 2,3-Difluoro-N-(3-methoxy-propyl)-N-[1-(2-piperidin-1-ylmethyl-benzyl)-1H-benzoimidazol-2-ylmethyl]-benzamide |
| 4. | | 2,3-Difluoro-N-[1-(2-piperidin-1-ylmethyl-benzyl)-1H-benzoimidazol-2-ylmethyl]-N-propyl-benzamide |
| 5. | | 2,3-Difluoro-N-isobutyl-N-[1-(2-piperidin-1-ylmethyl-benzyl)-1H-benzoimidazol-2-ylmethyl]-benzamide |
| 6. | | 2,3-Difluoro-N-methyl-N-[1-(2-piperidin-1-ylmethyl-benzyl)-1H-benzoimidazol-2-ylmethyl]-benzamide |

-continued

| | Compound | Name |
|---|---|---|
| 7. | | 2,4-Difluoro-N-isobutyl-N-[1-(2-piperidin-1-ylmethyl-benzyl)-1H-benzoimidazol-2-ylmethyl]-benzamide |
| 8. | | 2-Bromo-N-isobutyl-4,5-dimethoxy-N-[1-(2-piperidin-1-ylmethyl-benzyl)-1H-benzoimidazol-2-ylmethyl]-benzamide |
| 9. | | 2-Chloro-3,4-dimethoxy-N-(3-methyl-butyl)-N-[1-(2-morpholin-4-ylmethyl-benzyl)-1H-benzoimidazol-2-ylmethyl]-benzamide |
| 10. | | 2-Chloro-3,4-dimethoxy-N-(3-methyl-butyl)-N-[1-(2-piperidin-1-ylmethyl-benzyl)-1H-benzoimidazol-2-ylmethyl]-benzamide |

| Compound | Name |
|---|---|
| 11. | 2-Chloro-3,4-dimethoxy-N-(3-methyl-butyl)-N-[1-(2-pyrrolidin-1-ylmethyl-benzyl)-1H-benzoimidazol-2-ylmethyl]-benzamide |
| 12. | 2-Chloro-3,4-dimethoxy-N-(3-methyl-butyl)-N-{1-[2-(1H-tetrazol-5-yl)-benzyl]-1H-benzoimidazol-2-ylmethyl}-benzamide |
| 13. | 2-Chloro-3,4-dimethoxy-N-(3-methyl-butyl)-N-{1-[2-(4-methyl-piperazin-1-ylmethyl)-benzyl]-1H-benzoimidazol-2-ylmethyl}-benzamide |
| 14. | 2-Chloro-3,4-dimethoxy-N-(3-methyl-butyl)-N-{1-[2-(4-methyl-piperidin-1-ylmethyl)-benzyl]-1H-benzoimidazol-2-ylmethyl}-benzamide |

-continued

| Compound | Name |
| --- | --- |
| 15. | 2-chloro-4,5-dimethoxy-N-(3-methylbutyl)-N-[1-(2-piperidin-1-ylmethyl-benzyl)-1H-benzoimidazol-2-ylmethyl]-benzamide |
| 16. | 2-Chloro-N-(1-{2-[(ethyl-methyl-amino)-methyl]-benzyl}-1H-benzoimidazol-2-ylmethyl)-3,4-dimethoxy-N-(3-methyl-butyl)-benzamide |
| 17. | 2-Chloro-N-[1-(2-diethylaminomethyl-benzyl)-1H-benzoimidazol-2-ylmethyl]-3,4-dimethoxy-N-(3-methyl-butyl)-benzamide |
| 18. | 2-Chloro-N-{1-[2-(3,3-dimethyl-piperidin-1-ylmethyl)-benzyl]-1H-benzoimidazol-2-ylmethyl}-3,4-dimethoxy-N-(3-methyl-butyl)-benzamide |

| | Compound | Name |
|---|---|---|
| 19. | | 2-Chloro-N-isobutyl-N-[1-(2-piperidin-1-ylmethyl-benzyl)-1H-benzoimidazol-2-ylmethyl]-5-trifluoromethyl-benzamide |
| 20. | | 2-Chloro-N-isobutyl-N-[1-(2-piperidin-1-ylmethyl-benzyl)-1H-benzoimidazol-2-ylmethyl]-5-trifluoromethyl-benzamide |
| 21. | | 2-ethoxy-N-(3-methylbutyl)-N-[1-(2-piperidin-1-ylmethyl-benzyl)-1H-benzoimidazol-2-ylmethyl]-benzamide |
| 22. | | 2-phenyl-cyclopropanecarboxylic acid (3-methyl-butyl)-[1-(2-piperidin-1-ylmethyl-benzyl)-1H-benzoimidazol-2-ylmethyl]-amide |

-continued

| | Compound | Name |
|---|---|---|
| 23. | | 3-(2,3-difluorophenyl)-N-isobutyl-N-[1-(2-piperdin-1-ylmethyl-benzyl)-1H-benzoimidazol-2-ylmethyl]-acrylamide |
| 24. | | 3-(2,3-Difluoro-phenyl)-N-isopropyl-N-[1-(2-piperidin-1-ylmethyl-benzyl)-1H-benzoimidazol-2-ylmethyl]-acrylamide |
| 25. | | 3-(2,6-Dichloro-pheny1)-N-pentyl)-N-[1-(2-piperidin-1-ylmethyl-benzyl)-1H-benzoimidazol-2-ylmethyl]-acrylamide |
| 26. | | 3,6-Dichloro-benzo[b]thiophene-2-carboxylic acid butyl-[1-(2-piperidin-1-ylmethyl-benzyl)-1H-benzoimidazol-2-ylmethyl]-amide |

-continued

| Compound | Name |
|---|---|
| 27. | 3-Bromo-5-chloro-thiophene-2-sulfonic acid butyl-[1-(2-piperidin-1-ylmethyl-benzyl)-1H-benzoimidazol-2-ylmethyl]-amide |
| 28. | 3-Chloro-benzo[b]thiophene-2-carboxylic acid (2-dimethylamino-ethyt)-[1-(2-piperidin-1-ylmethyl-benzyl)-1H-benzoimidazol-2-ylmethyl]-amide |
| 29. | 3-Chloro-benzo[b]thiophene-2-carboxylic acid (2-methoxy-ethyl)-[1-(2-piperidin-1-ylmethyl-benzyl)-1H-benzoimidazol-2-ylmethyl]-amide |
| 30. | 3-Chloro-benzo[b]thiophene-2-carboxylic acid (3-methoxy-propyl)-[1-(2-piperidin-1-ylmethyl-benzyl)-1H-benzoimidazol-2-ylmethyl]-amide |

-continued

| Compound | Name |
|---|---|
| 31. | 3-Chloro-benzo[b]thiophene-2-carboxylic acid (3-methyl-butyl)-[1-(2-piperidin-1-ylmethyl-benzyl)-1H-benzoimidazol-2-ylmethyl]-amide |
| 32. | 3-Chloro-benzo[b]thiophene-2-carboxylic acid [1-(2-azepan-1-ylmethyl-benzyl)-1H-benzoimidazol-2-ylmethyl]-butyl-amide |
| 33. | 3-chloro-benzo[b]thiophene-2-carboxylic acid [1-(2-piperdin-1-ylmethyl-benzyl)-1H-benzoimidazol-2-ylmethyl]-propylamide |
| 34. | 3-Chloro-benzo[b]thiophene-2-carboxylic acid butyl-[1-(2-imidazol-1-ylmethyl-benzyl)-1H-benzoimidazol-2-ylmethyl]-amide |

| Compound | Name |
|---|---|
| 35. | 3-chloro-benzo[b]thiophene-2-carboxylic acid butyl-[1-(2-piperidin-1-ylmethyl-benzyl)-1H-benzoimidazol-2-ylmethyl]-amide |
| 36. | 3-Chloro-benzo[b]thiophene-2-carboxylic acid butyl-[1-(2-piperidin-1-ylmethyl-benzyl)-5-trifluoromethyl-1H-benzoimidazol-2-ylmethyl]-amide |
| 37. | 3-Chloro-benzo[b]thiophene-2-carboxylic acid butyl-[1-(2-piperidin-1-ylmethyl-benzyl)-1H-benzoimidazol-2-ylmethyl]-amide |
| 38. | 3-Chloro-benzo[b]thiophene-2-carboxylic acid butyl-[1-(2-pyrrolidin-1-ylmethyl-benzyl)-1H-benzoimidazol-2-ylmethyl]-amide |

-continued

| Compound | Name |
|---|---|
| 39. | 3-Chloro-benzo[b]thiophene-2-carboxylic acid butyl-[5-cyano-1-(2-piperidin-1-ylmethyl-benzyl)-1H-benzoimidazol-2-ylmethyl]-amide |
| 40. | 3-Chloro-benzo[b]thiophene-2-carboxylic acid butyl-{1-[1-(2-piperidin-1-ylmethyl-benzyl)-1H-benzoimidazol-2-yl]-ethyl}-amide |
| 41. | 3-Chloro-benzo[b]thiophene-2-carboxylic acid butyl-{1-[1-(2-piperidin-1-ylmethyl-phenyl)-ethyl]-1H-benzoimidazol-2-ylmethyl}-amide |
| 42. | 3-Chloro-benzo[b]thiophene-2-carboxylic acid butyl-{1-[2-(2-methyl-piperidin-1-ylmethyl)-benzyl]-1H-benzoimidazol-2-ylmethyl}-amide |

| Compound | | Name |
|---|---|---|
| 43. | 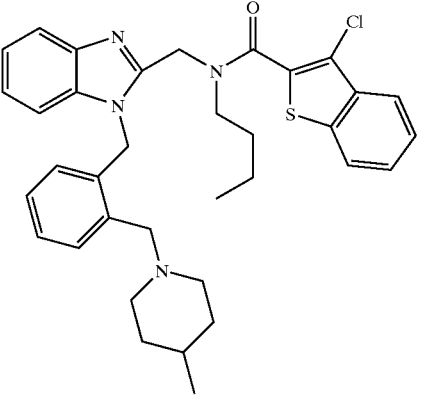 | 3-Chloro-benzo[b]thiophene-2-carboxylic acid butyl-{1-[2-(4-methyl-piperidin-1-ylmethyl)-benzyl]-1H-benzoimidazol-2-ylmethyl}-amide |
| 44. | 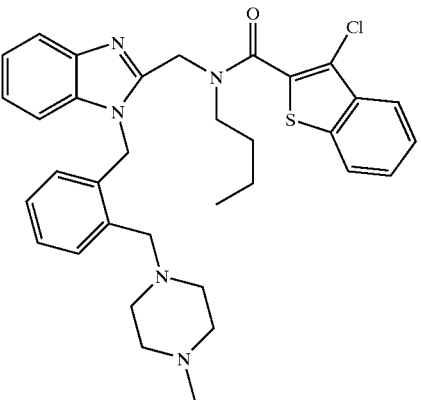 | 3-Chloro-benzo[b]thiophene-2-carboxylic acid butyl-{1-[2-(4-methyl-piperazin-1-ylmethyl)-benzyl]-1H-benzoimidazol-2-ylmethyl}-amide |
| 45. | 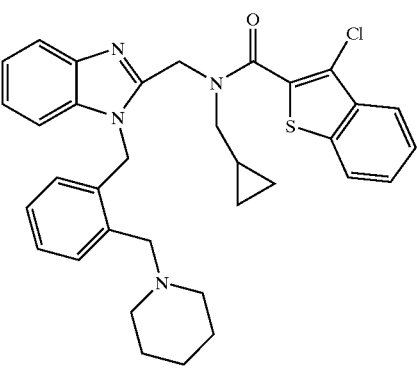 | 3-chloro-benzo[b]thiophene-2-carboxylic acid cyclopropylmethyl-[1-(2-piperdin-1-ylmethyl-benzyl)-1H-benzoimidazol-2-ylmethyl]-amide |
| 46. | 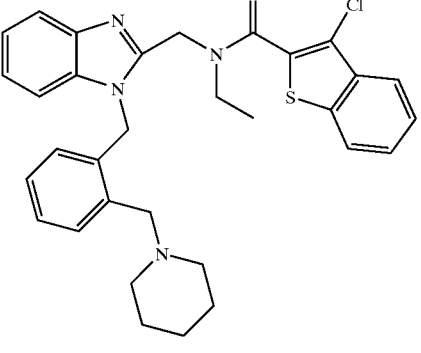 | 3-Chloro-benzo[b]thiophene-2-carboxylic acid ethyl-[1-(2-piperidin-1-ylmethyl-benzyl)-1H-benzoimidazol-2-ylmethyl]-amide |

| Compound | Name |
|---|---|
| 47. 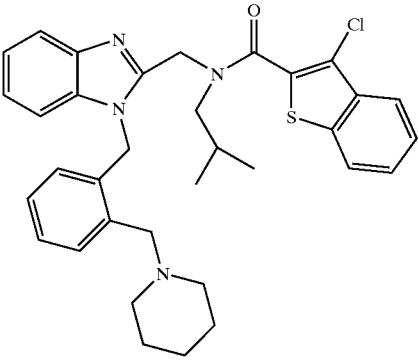 | 3-Chloro-benzo[b]thiophene-2-carboxylic acid isobutyl-[1-(2-piperidin-1-ylmethyl-benzyl)-1H-benzoimidazol-2-ylmethyl]-amide |
| 48. 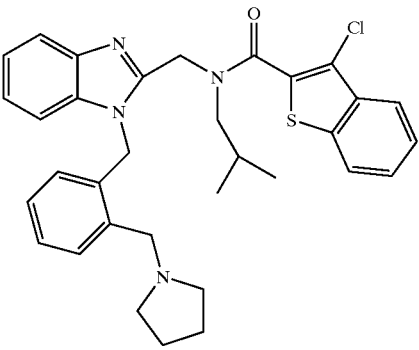 | 3-chloro-benzo[b]thiophene-2-carboxylic acid isobutyl-[1-(2-pyrrolidin-1-ylmethyl-benzyl)-1H-benzoimidazol-2-ylmethyl]-amide |
| 49. 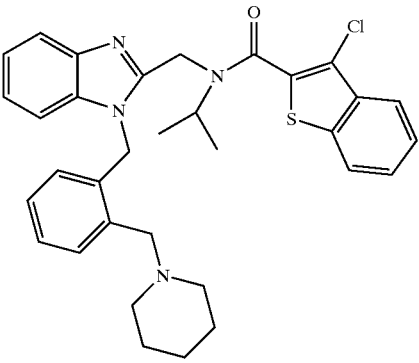 | 3-Chloro-benzo[b]thiophene-2-carboxylic acid isopropyl-[1-(2-piperidin-1-ylmethyl-benzyl)-1H-benzoimidazol-2-ylmethyl]-amide |
| 50. 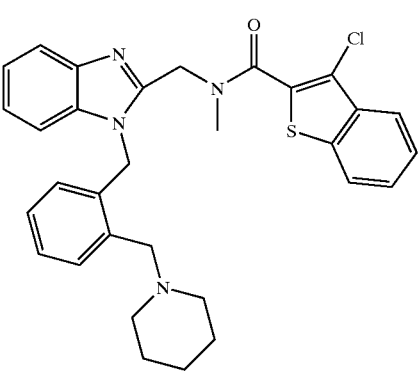 | 3-Chloro-benzo[b]thiophene-2-carboxylic acid methyl-[1-(2-piperidin-1-ylmethyl-benzyl)-1H-benzoimidazol-2-ylmethyl]-amide |

| Compound | Name |
|---|---|
| 51. | 3-chloro-thiophene-2-carboxylic acid butyl-[1-(2-pyrrolidin-1-ylmethyl-benzyl)-1H-benzoimidazol-2-ylmethyl]-amide |
| 52. | 4,5-dichloro-isothiazole-3-carboxylic acid isobutyl-[1-(2-piperidin-1-ylmethyl-benzyl)-1H-benzoimidazol-2-ylmethyl]-amide |
| 53. | 4-Bromo-N-butyl-N-[1-(2-piperidin-1-ylmethyl-benzyl)-1H-benzoimidazol-2-ylmethyl]-benzamide |
| 54. | 4-Chloro-N-isobutyl-N-[1-(2-piperidin-1-ylmethyl-benzyl)-1H-benzoimidazol-2-ylmethyl]-benzamide |

| Compound | Name |
|---|---|
| 55. | 5-Chloro-3-methyl-benzo[b]thiophene-2-sulfonic acid butyl-[1-(2-piperidin-1-ylmethyl-benzyl)-1H-benzoimidazol-2-ylmethyl]-amide |
| 56. | 5-Chloro-thiophene-2-sulfonic acid butyl-[1-(2-piperidin-1-ylmethyl-benzyl)-1H-benzoimidazol-2-ylmethyl]-amide |
| 57. | 6-Chloro-imidazo[2,1-b]thiazole-5-sulfonic acid butyl-[1-(2-piperidin-1-ylmethyl-benzyl)-1H-benzoimidazol-2-ylmethyl]-amide |
| 58. | 8-bromo-naphthalene-1-carboxylic acid butyl-[1-(2-piperidin-1-ylmethyl-benzyl)-1H-benzoimidazol-2-ylmethyl]-amide |

| | Compound | Name |
|---|---|---|
| 59. | | 8-Iodo-naphthalene-1-carboxylic acid butyl-[1-(2-piperidin-1-ylmethyl-benzyl)-1H-benzoimidazol-2-ylmethyl]-amide |
| 60. | | Butyl-(2,3-difluoro-benzyl)-[1-(2-piperidin-1-ylmethyl-benzyl)-1H-benzoimidazol-2-ylmethyl]-amine |
| 61. | | Butyl-(2,3-difluoro-benzyl)-{1-[1-(2-piperidin-1-ylmethyl-benzyl)-1H-benzoimidazol-2-yl]-ethyl}-amine |
| 62. | | N-(3-Methyl-butyl)-N-[1-(2-piperidin-1-ylmethyl-benzyl)-1H-benzoimidazol-2-ylmethyl]-4-trifluoromethoxy-benzamide |

| | Compound | Name |
|---|---|---|
| 63. | | N-[1-(4-hexamethyleneimin-1-yl-but-2-enyl)-1H-benzoimidazol-2-ylmethyl]-N-butyl-2,3-difluoro-benzamide |
| 64. | | naphthalene-1-carboxylic acid isobutyl-[1-(2-piperidin-1-ylmethyl-benzyl)-1H-benzoimidazol-2-ylmethyl]-amide |
| 65. | | N-butyl-2,3-difluoro-N-[1-(2-piperidin-1-ylmethyl-benzyl)-1H-benzoimidazol-2-ylmethyl]-benzamide |
| 66. | | N-Butyl-2,3-difluoro-N-[1-(2-piperidin-1-ylmethyl-benzyl)-1H-imidazo[4,5-c]pyridin-2-ylmethyl]-benzamide |

-continued

| | Compound | Name |
|---|---|---|
| 67. | | N-Butyl-2,3-difluoro-N-[1-(2-piperidin-1-ylmethyl-benzyl)-5-trifluoromethyl-1H-benzoimidazol-2-ylmethyl]-benzamide |
| 68. | | N-butyl-2,3-difluoro-N-[1-(4-morpholin-4-yl-but-2-enyl)-1H-benzoimidazol-2-ylmethyl]-benzamide |
| 69. | | N-butyl-2,3-difluoro-N-[1-(4-piperidin-1-yl-but-2-enyl)-1H-benzoimidazol-2-ylmethyl]-benzamide |
| 70. | | N-butyl-2,3-difluoro-N-[1-(4-pyrrolidin-1-yl-but-2-enyl)-1H-benzoimidazol-2-ylmethyl]-benzamide |

-continued

| | Compound | Name |
|---|---|---|
| 71. | | N-Butyl-2,3-difluoro-N-{1-[1-(2-piperidin-1-ylmethyl-benzyl)-1H-benzoimidazol-2-yl]-ethyl}-benzamide |
| 72. | | N-Butyl-2,3-difluoro-N-{1-[1-(2-piperidin-1-ylmethyl-phenyl)-ethyl]-1H-benzoimidazol-2-ylmethyl}-benzamide |
| 73. | | N-butyl-2,3-difluoro-N-{1-[4-(4-methyl-piperidin-1-yl)-but-2-enyl]-1H-benzoimidazol-2-ylmethyl}-benzamide |
| 74. | | N-Butyl-2,4-difluoro-N-[1-(2-piperidin-1-ylmethyl-benzyl)-1H-benzoimidazol-2-ylmethyl]-benzamide |

-continued

| Compound | Name |
|---|---|
| 75. | N-butyl-2,5-dichloro-N-[1-(2-piperidin-1-ylmethyl-benzyl)-1H-benzoimidazol-2-ylmethyl]-benzamide |
| 76. | N-butyl-2-chloro-3,4-dimethoxy-N-[1-(2-piperidin-1-ylmethyl-benzyl)-1H-benzoimidazol-2-ylmethyl]-benzamide |
| 77. | N-Butyl-2-chloro-N-[1-(2-piperidin-1-ylmethyl-benzyl)-1H-benzoimidazol-2-ylmethyl]-5-trifluoromethyl-benzamide |
| 78. | N-Butyl-2-chloro-N-[1-(2-piperidin-1-ylmethyl-benzyl)-1H-benzoimidazol-2-ylmethyl]-5-trifluoromethyl-benzamide |

-continued

| | Compound | Name |
|---|---|---|
| 79. | | N-Butyl-2-methyl-5-fluoro-N-[1-(2-piperidin-1-ylmethyl-benzyl)-1H-benzoimidazol-2-ylmethyl]-benzamide |
| 80. | | N-Butyl-3-(2,3-difluoro-phenyl)-N-[1-(2-piperidin-1-ylmethyl-benzyl)-1H-benzoimidazol-2-ylmethyl]-acrylamide |
| 81. | | N-Butyl-3,4-difluoro-N-[1-(2-piperidin-1-ylmethyl-benzyl)-1H-benzoimidazol-2-ylmethyl]-benzamide |
| 82. | | N-Butyl-3-chloro-4-methoxy-N-[1-(2-piperidin-1-ylmethyl-benzyl)-1H-benzoimidazol-2-ylmelhyl]-benzamide |

| | Compound | Name |
|---|---|---|
| 83. | | N-butyl-3-fluoro-4-methoxy-N-[1-(2-piperidin-1-ylmethyl-benzyl)-1H-benzoimidazol-2-ylmethyl]-benzamide |
| 84. | | N-Butyl-3-fluoro-4-methyl-N-[1-(2-piperidin-1-ylmethyl-benzyl)-1H-benzoimidazol-2-ylmethyl]-benzamide |
| 85. | | N-Butyl-3-fluoro-4-methyl-N-[1-(2-piperidin-1-ylmethyl-benzyl)-1H-benzoimidazol-2-ylmethyl]-benzamide |
| 86. | | N-Butyl-3-fluoro-N-[1-(2-piperidin-1-ylmethyl-benzyl)-1H-benzoimidazol-2-ylmethyl]-benzamide |

-continued

| Compound | Name |
|---|---|
| 87. | N-butyl-4-chloro-N-[1-(2-piperidin-1-ylmethyl-benzyl)-1H-benzoimidazol-2-ylmethyl]-benzamide |
| 88. | N-Butyl-4-chloro-N-[1-(2-piperidin-1-ylmethyl-benzyl)-1H-benzoimidazol-2-ylmethyl]-benzenesulfonamide |
| 89. | N-Butyl-4-cyano-N-[1-(2-piperidin-1-ylmethyl-benzyl)-1H-benzoimidazol-2ylmethyl]-benzamide |
| 90. | N-Butyl-4-ethoxy-N-[1-(2-piperidin-1-ylmethyl-benzyl)-1H-benzoimidazol-2-ylmethyl]-benzamide |

-continued

| | Compound | Name |
|---|---|---|
| 91. | | N-Butyl-4-ethylaminomethyl-N-[1-(2-piperidin-1-ylmethyl-benzyl)-1H-benzoimidazol-2-ylmethyl]-benzamide |
| 92. | | N-Butyl-4-fluoro-N-[1-(2-piperidin-1-ylmethyl-benzyl)-1H-benzoimidazol-2-ylmethyl]-benzenesulfonamide |
| 93. | | N-Butyl-4-methanesulfonyl-N-[1-(2-piperidin-1-ylmethyl-benzyl)-1H-benzoimidazol-2-ylmethyl]-benzamide |
| 94. | | N-Butyl-4-methylaminomethyl-N-[1-(2-piperidin-1-ylmethyl-benzyl)-1H-benzoimidazol-2-ylmethyl]-benzamide |

| Compound | Name |
|---|---|
| 95. | N-butyl-4-methylsulfanyl-N-[1-(2-piperidin-1-ylmethyl-benzyl)-1H-benzoimidazol-2-ylmethyl]-benzamide |
| 96. | N-Butyl-4-methylsulfanyl-N-[1-(2-piperidin-1-ylmethyl-benzyl)-1H-benzoimidazol-2-ylmethyl]-benzamide |
| 97. | N-Butyl-4-morpholin-4-ylmethyl-N-[1-(2-piperidin-1-ylmethyl-benzyl)-1H-benzoimidazol-2-ylmethyl]-benzamide |
| 98. | N-Butyl-4-pentyloxy-N-[1-(2-piperidin-1-ylmethyl-benzyl)-1H-benzoimidazol-2-ylmethyl]-benzamide |

-continued

| | Compound | Name |
|---|---|---|
| 99. | | N-Butyl-4-piperidin-1-ylmethyl-N-[1-(2-piperidin-1-ylmethyl-benzyl)-1H-benzoimidazol-2-ylmethyl]-benzamide |
| 100. | | N-Butyl-5-fluoro-2-methyl-N-[1-(2-piperidin-1-ylmethyl-benzyl)-1H-benzoimidazol-2-ylmethyl]-benzenesulfonamide |
| 101. | | N-Butyl-N-[1-(2-piperidin-1-ylmethyl-benzyl)-1H-benzoimidazol-2-ylmethyl]-3-o-tolyl-acrylamide |
| 102. | | N-Butyl-N-[1-(2-piperidin-1-ylmethyl-benzyl)-1H-benzoimidazol-2-ylmethyl]-4-trifluoromethylsulfanyl-benzamide |

-continued

| | Compound | Name |
|---|---|---|
| 103. | 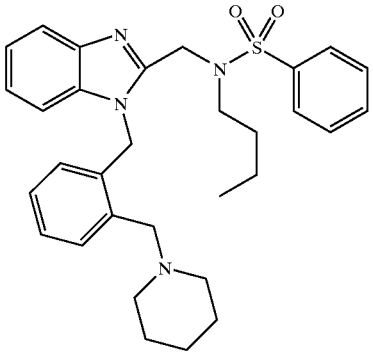 | N-Butyl-N-[1-(2-piperidin-1-ylmethyl-benzyl)-1H-benzoimidazol-2-ylmethyl]-benzenesulfonamide |
| 104. | 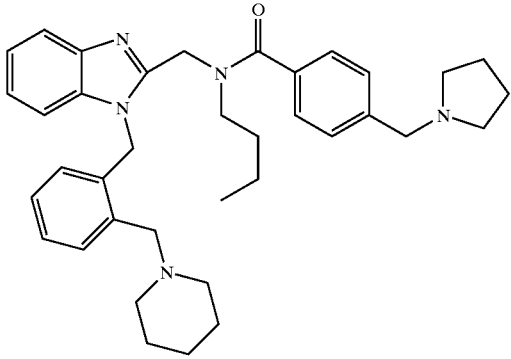 | N-Butyl-N-[1-(2-piperidin-1-ylmethyl-benzyl)-1H-benzoimidazol-2-ylmethyl]-4-pyrrolidin-1-ylmethyl-benzamide |
| 105. | 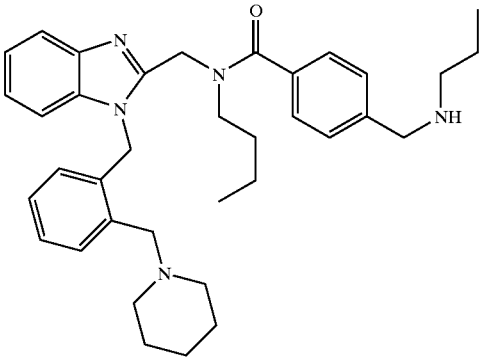 | N-Butyl-N-[1-(2-piperidin-1-ylmethyl-benzyl)-1H-benzoimidazol-2-ylmethyl]-4-propylaminomethyl-benzamide |
| 106. | 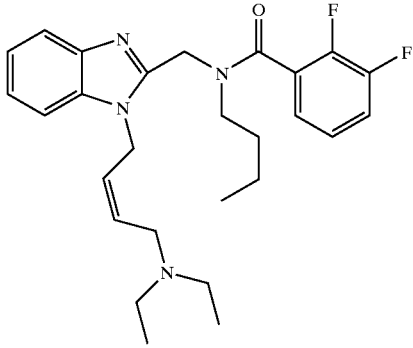 | N-butyl-N-[1-(4-diethylamino-but-2-enyl)-1H-benzoimidazol-2-ylmethyl]-2,3-difluoro-benzamide |

| Compound | Name |
|---|---|
| 107. | N-Butyl-N-[5-cyano-1-(2-piperidin-1-ylmethyl-benzyl)-1H-benzoimidazol-2-ylmethyl]-2,3-difluoro-benzamide |
| 108. | N-cyclopropylmethyl-2,3-difluoro-N-[1-(2-piperdin-1-ylmethyl-benzyl)-1H-benzoimidazol-2-ylmethyl]-benzamide |
| 109. | N-cyclopropylmethyl-4-methylsulfanyl-N-[1-(2-piperidin-1-ylmethyl-benzyl)-1H-benzoimidazol-2-ylmethyl]-benzamide |
| 110. | N-Cyclopropylmethyl-N-[1-(2-piperidin-1-ylmethyl-benzyl)-1H-benzoimidazol-2-ylmethyl]-4-trifluoromethylsulfanyl-benzamide |

| Compound | Name |
|---|---|
| 111. | N-Ethyl-2,3-difluoro-N-[1-(2-piperidin-1-ylmethyl-benzyl)-1H-benzoimidazol-2-ylmethyl]-benzamide |
| 112. | N-isobutyl-3-naphthalen-1-yl-N-[1-(2-piperdin-1-ylmethyl-benzyl)-1H-benzoimidazol-2-ylmethyl]-acrylamide |
| 113. | N-Isobutyl-4-pentyloxy-N-[1-(2-piperidin-1-ylmethyl-benzyl)-1H-benzoimidazol-2-ylmethyl]-benzamide |
| 114. | N-isobutyl-N-[1-(2-piperdin-1-ylmethyl-benzyl)-1H-benzoimidazol-2-ylmethyl]-3-o-tolyl-acrylamide |

-continued

| Compound | Name |
|---|---|
| 115. | N-Isobutyl-N-[1-(2-piperidin-1-ylmethyl-benzyl)-1H-benzoimidazol-2-ylmethyl]-benzamide |
| 116. | N-Isopropyl-N-[1-(2-piperidin-1-ylmethyl-benzyl)-1H-benzoimidazol-2-ylmethyl]-benzamide |
| 117. | N-Isopropyl-N-[1-(2-piperidin-1-ylmethyl-benzyl)-1H-benzoimidazol-2-ylmethyl]-3-o-tolyl-acrylamide |
| 118. | N-propyl-2,3-difluoro-N-[1-(2-piperidin-1-ylmethyl-benzyl)-1H-benzoimidazol-2-ylmethyl]-benzamide |

Example 3

Melanin Concentrating Hormone Receptor Binding Assay

This Example illustrates a standard assay of melanin concentrating hormone receptor binding that may be used to determine the binding affinity of compounds for the MCH receptor.

Total RNA was prepared from cynomolgus macaque hypothalamus. Monkey hypothalamic cDNA was prepared using random primers and reverse transcriptase according to standard methods. A cDNA encoding the monkey MCH1 receptor was obtained via PCR amplification using the forward (5') Primer of SEQ ID NO:3 and the reverse (3') Primer of SEQ ID NO:4. The full length PCR product was initially cloned into the vector pCR 2.1 (Invitrogen, Carlsbad, Calif.). The cDNA was reamplified using a forward primer engineered to include an optimal translation initiation site (Kozak sequence). A cDNA expression cassette fragment encoding the monkey MCH1 receptor was blunt end ligated into the PCR-SCRIPT vector (STRATAGENE, La Jolla, Calif.). The receptor sequence was excised from this vector using EcoRI and Not I and subcloned into the EcoRI/Not site of PcDNA3.1 (INVITROGEN Corp., Carlsbad, Calif.). The MCH1 receptor DNA sequence is provided in SEQ ID NO:1, with the encoded amino acid sequence provided in SEQ ID NO:2.

HEK 293 cells (American Type Culture Collection, Manassas, Va.) were stably transfected with the MCH receptor expression vector via standard calcium phosphate precipitation, and were grown to confluency (approximately 48–72 hours) in DMEM high glucose culture medium (catalog #10–017-CV, MEDIATECH, Herndon, Va.) supplemented with 10% fetal bovine serum and 25 mM.HEPES, and 500 $\mu$g/ml G418, for 48–72 hours at 37° C., 5% $CO_2$. The cells were pelleted by gentle centrifugation. Cell pellets were washed twice with cold PBS, harvested in cold PBS containing 5 mM EDTA, and stored at −80° C.

At the time of assay, pellets were thawed by addition of wash buffer (25 mM Hepes with 1.0 mM $CaCl_2$, 5.0 mM $MgCl_2$, 120 mM NaCl, PH7.4) and homogenized for 30 seconds using a BRINKMAN POLYTRON, setting 5. Cells were centrifuged for 10 minutes at 48,000×g. The supernatant was discarded and the pellet was resuspended in fresh wash buffer, and homogenized again. An aliquot of this membrane homogenate was used to determine protein concentration via the Bradford method (BIO-RAD Protein Assay Kit, #500-0001, BIO-RAD, Hercules, Calif.). By this measure, a 1-liter culture of cells typically yields 50–75 mg of total membrane protein. The homogenate was centrifuged as before and resuspended to a protein concentration of 333 $\mu$g/ml in binding buffer (Wash buffer+0.1% BSA and 1.0 $\mu$M final phosphoramidon) for an assay volume of 50 $\mu$g membrane protein/150 $\mu$l binding buffer. Phosphoramidon was from SIGMA BIOCHEMICALS, St. Louis, Mo. (cat# R-7385).

Competition binding assays were performed at room temperature in Falcon 96 well round bottom polypropylene plates. Each assay well contained 150 $R_1$ of MCH receptor containing membranes prepared as described above, 50 $\mu$l $^{125}$I-Tyr MCH, 50 $R_1$ binding buffer, and 2 $\mu$l test compound in DMSO. $^{125}$I-Tyr MCH (specific activity=2200 Ci/mMol) is purchased from NEN, Boston, Mass. (Cat #NEX 373) and was diluted in binding buffer to provide a final assay concentration of 30 pM.

Non-specific binding was defined as the binding measured in the presence of 1 $\mu$M unlabeled MCH. MCH is purchased from BACHEM U.S.A., King of Prussia, Pa. (cat #II-1482). Assay wells used to determine MCH binding contained 150 $\mu$l of MCH receptor containing membranes, 50 $\mu$l $^{125}$I-Tyr MCH, 25 $\mu$l binding buffer, and 25 $\mu$l binding buffer.

Assay plates were incubated for 1 hour at room temperature. Membranes were harvested onto WALLAC™ glass fiber filters (PERKIN-ELMER, Gaithersburg, Md.) which were pre-soaked with 1.0% PEI (polyethyleneimine) for 2 hours prior to use. Filters were allowed to dry overnight, and then counted in a WALLAC 1205 BETA PLATE counter after addition of WALLAC BETA SCINT™ scintillation fluid.

For saturation binding, the concentration of $^{125}$I-Tyr MCH was varied from 7 to 1,000 pM. Typically, 11 concentration points were collected per saturation binding curve. Equilibrium binding parameters were determined by fitting the allosteric Hill equation to the measured values with the aid of the computer program FitP™ (BIOSOFT, Ferguson, Mo.). For the compounds described herein, $K_i$ values were below 1 micromolar, preferably below 500 nanomolar, more preferably below 100 nanomolar.

Example 4

Calcium Mobilization Assay

This Example illustrates a representative functional assay for monitoring the response of cells expressing melanin concentrating hormone receptors to melanin concentrating hormone. This assay can also be used to determine if test compounds act as agonists or antagonists of melanin concentrating hormone receptors.

Chinese Hamster Ovary (CHO) cells (American Type Culture Collection; Manassas, Va.) were stably transfected with the MCH expression vector described in Example 2 via calcium phosphate precipitation, and were grown to a density of 15,000 cells/well in FALCON™ black-walled, clear-bottomed 96-well plates (#3904, BECTON-DICKINSON, Franklin Lakes, N.J.) in Ham's F12 culture medium (MEDIATECH, Herndon, Va.) supplemented with 10% fetal bovine serum, 25 mM HEPES and 500 $\mu$g/mL (active) G418. Prior to running the assay, the culture medium was emptied from the 96 well plates. Fluo-3 calcium sensitive dye (Molecular Probes, Eugene, Oreg.) was added to each well (dye solution: 1 mg FLUO-3 AM, 440 $\mu$L DMSO and 440 $\mu$l 20% pluronic acid in DMSO, diluted 1:4, 50 $R_1$ diluted solution per well). Plates were covered with aluminum foil and incubated at 37° C. for 1–2 hours. After the incubation, the dye was emptied from the plates, cells were washed once in 100 $\mu$l KRH buffer (0.05 mM KCl, 0.115 M NaCl, 9.6 mM $NaH_2PO_4$, 0.01 mM $MgSO_4$, 25 mM HEPES, pH 7.4) to remove excess dye; after washing, 80 $\mu$l KRH buffer was added to each well.

Fluorescence response was monitored upon the addition of either human MCH receptor or test compound by a FLIPR™ plate reader (Molecular Devices, Sunnyvale, Calif.) by excitation at 480 nM and emission at 530 nM.

In order to measure the ability of a test compound to antagonize the response of cells expressing MCH receptors to MCH, the $EC_{50}$ of MCH was first determined. An additional 20 $\mu$l of KRH buffer and 1 $\mu$l DMSO was added to each well of cells, prepared as described above. 100 $\mu$l human MCH in KRH buffer was automatically transferred by the FLIPR instrument to each well. An 8-point concentration response curve, with final MCH concentrations of 1 nM to 3 FM, was used to determine MCH $EC_{50}$.

Test compounds were dissolved in DMSO, diluted in 20 $\mu$l KRH buffer, and added to cells prepared as described above. The 96 well plates containing prepared cells and test compounds were incubated in the dark, at room temperature for 0.5–6 hours. It is important that the incubation not continue beyond 6 hours. Just prior to determining the fluorescence response, 100 μl human MCH diluted in KRH buffer to $2 \times EC_{50}$ was automatically added by the FLIPR instrument to each well of the 96 well plate for a final sample volume of 200 μl and a final MCH concentration of $EC_{50}$. The final concentration of test compounds in the assay wells was between 1 μM and 5 μM. Typically, cells exposed to one $EC_{50}$ of MCH exhibit a fluorescence response of about 10,000 Relative Fluorescence Units. Antagonists of the MCH receptor exhibit a response that is significantly less than that of the control cells to the $p \leq 0.05$ level, as measured using a parametric test of statistical significance. Typically, antagonists of the MCH receptor preferably by at least 80% as compared to matched controls.

The ability of a compound to act as an agonist of the MCH receptor was determined by measuring the fluorescence response of cells expressing MCH receptors, using the methods described above, in the absence of MCH. Compounds that cause cells to exhibit fluorescence above background are MCH receptor agonists.

Example 5

Determination of $D_2$ and $D_4$ Receptor Binding Activity

This Example illustrates a representative standard assay for determining the binding affinity of compounds to dopamine $D_4$ and $D_2$ receptors.

Pellets of Chinese hamster ovary (CHO) cells containing recombinantly expressing primate $D_2$, human $D_4$ dopamine receptors were used for the assays. The sample was homogenized in 100 volumes (w/vol) of 0.05 M Tris HCl buffer containing 120 mM NaCl, 5 mM $MgCl_2$ and 1 mM EDTA at 4° C. and pH 7.4. The sample was then centrifuged at 30,000×g and resuspended and rehomogenized. The sample was then centrifuged as described and the final tissue sample was frozen until use. The tissue was resuspended 1:20 (wt/vol) in 0.05 M Tris HCl buffer containing 120 mM NaCl.

Incubations for dopaminergic binding are carried out at 25° C. and contain 0.4 ml of tissue sample, 0.1 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Nonspecific binding was defined as that binding found in the presence of 1 micromolar spiperone; without further additions, nonspecific binding was less than 20% of total binding.

Example 6

Determination of Human Bradykinin $B_2$ Receptor Binding Activity

This Example illustrates a representative standard assay for determining the binding affinity of compounds to human bradykinin $B_2$ receptor.

Baculovirus-infected Sf9 cells expressing recombinant human bradykinin $B_2$ receptors are harvested 48 hours post infection via centrifugation at 3000×g. Cells are washed with ice-cold PBS and stored at −70° C. until needed. Frozen cell pellets are resuspended in ice cold washing buffer (50 mM Tris pH 7.0) and homogenized via POLYTRON for 30 seconds at setting 5. membranes are centrifuged at 40,000×g for 10 minutes. Pellets are resuspended in washing buffer with the aid of a polytron and centrifuged again. Membranes are resuspended in binding buffer at a concentration of 133 μg/mL. This corresponds to 20 μg of protein per 150 μL.

When measuring non-specific binding, incubations contain 150 μL of Sf9 cell membranes, 50 μL $^3$H-bradykinin (0.25 nM), 25 μL unlabeled bradykinin at 1 μM final concentration and 2 μL DMSO. Incubations for determining test compound binding contain 175 μL of Sf9 cell membranes, 50 μL $^3$H-bradykinin (0.25 nM) and test compound in 2 μL DMSO. The concentration of the test compound is generally 1 μM for displacement studies. Binding buffer is 50 mM Tris pH 7.0, 0.14 grams per liter bacatracin (approx. 50,000 units of activity/liter; Amersham) and $10^{-6}$ M captopril (Sigma).

The binding reaction components are incubated for 2 hours at 4° C. in Falcon U bottom plates. Plates are harvested on the microbeta harvester onto 0.5% PEI pretreated unifilters. After harvesting, filters are dried overnight. 17 μL of beta-scint is added to each well before the unifilters are counted in the microbeta counter. Data are collected in duplicate determinations, averaged and % inhibition of total specific binding is calculated. Total Specific Binding=Total Binding−Nonspecific Binding. In some cases, the amounts of unlabeled drug are varied and total displacement curves of binding are carried out. Ki is determined by the Cheng-Prusoff equation (Cheng and Prusoff (1972) *Biochem. Pharmacol.* 22:3099–3108). Compounds that do not substantially bind human bradykinin $B_2$ receptor generally have Ki's>1 micromolar.

Example 7

MDCK Cytotoxicity Assay

This Example illustrates the evaluation of compound toxicity using a Madin Darby canine kidney (MDCK) cell cytotoxicity assay.

1 μL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog #30-2003). 100 μL of diluted cells is added to each well, except for five standard curve control wells that contain 100 μL of warm medium without cells. The plate is then incubated at 37° C. under 95% $O_2$, 5% $CO_2$ for 2 hours with constant shaking. After incubation, 50 μL of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOP-COUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 pM of a preferred test compound exhibit ATP levels that are at least 80%, preferably at least 90%, of the untreated cells. When a 100 FM concentration of the test compound is used, cells treated with preferred test compounds exhibit ATP levels that are at least 50%, preferably at least 80%, of the ATP levels detected in untreated cells.

Example 8

Microsomal in vitro Half-Life

This Example illustrates the evaluation of compound half-life values ($t_{1/2}$ values) using a representative liver microsomal half-life assay.

Pooled human liver microsomes are obtained from Xeno-Tech LLC, 3800 Cambridge St., Kansas City, Kans. 66103 (catalog #H0610). Such liver microsomes may also be obtained from In Vitro Technologies (Baltimore, Md.) or Tissue Transformation Technologies (Edison, N.J.). Six test reactions are prepared, each containing 25 µl microsomes, 5 µl of a 100 µM solution of test compound, and 399 µl 0.1 M phosphate buffer (19 mL 0.1 M $NaH_2PO_4$, 81 mL 0.1 M $Na_2HPO_4$, adjusted to pH 7.4 with $H_3PO_4$). A seventh reaction is prepared as a positive control containing 25 µl microsomes, 399 µl 0.1 M phosphate buffer, and 5 µl of a 100 µM solution of a compound with known metabolic properties (e.g., DIAZEPAM or CLOZEPINE). Reactions are preincubated at 39° C. for 10 minutes.

CoFactor Mixture is prepared by diluting 16.2 mg NADP and 45.4 mg Glucose-6-phosphate in 4 mL 100 mM $MgCl_2$. Glucose-6-phosphate dehydrogenase solution is prepared by diluting 214.3 µl glucose-6-phosphate dehydrogenase suspension (Boehringer-Manheim catalog no. 0737224, distributed by Roche Molecular Biochemicals, Indianapolis, Ind.) into 1285.7 µl distilled water. 71 µl Starting Reaction Mixture (3 mL CoFactor Mixture; 1.2 mL Glucose-6-phosphate dehydrogenase solution) is added to 5 of the 6 test reactions and to the positive control. 71 µl 100 mM $MgCl_2$ is added to the sixth test reaction, which is used as a negative control. At each time point (0, 1, 3, 5, and 10 minutes), 75 µl of each reaction mix is pipetted into a well of a 96-well deep-well plate containing 75 µl ice-cold acetonitrile. Samples are vortexed and centrifuged 10 minutes at 3500 rpm (Sorval T 6000D centrifuge, H1000B rotor). 75 µl of supernatant from each reaction is transferred to a well of a 96-well plate containing 150 µl of a 0.5 µM solution of a compound with a known LCMS profile (internal standard) per well. LCMS analysis of each sample is carried out and the amount of unmetabolized test compound is measured as AUC, compound concentration vs. time is plotted, and the $t_{1/2}$ value of the test compound is extrapolated.

Preferred compounds of the present invention exhibit in vitro $t_{1/2}$ values of greater than 10 minutes and less than 4 hours, preferably between 30 minutes and 1 hour, in human liver microsomes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the formula:

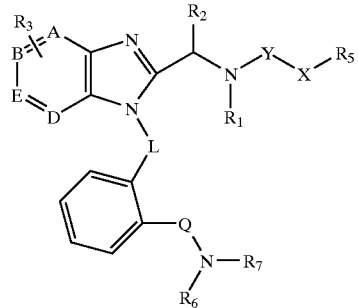

or a pharmaceutically acceptable salt thereof, wherein:

A, B, E and D each represent CH;

$R_1$ is:
(i) —C(=O)NH$_2$, —SO$_2$NH$_2$ or —COOH;
(ii) $C_1$–$C_8$alkyl, $C_2$–$C_8$alkenyl, $C_2$–$C_8$alkynyl, $C_2$–$C_8$alkanoyl, $C_2$–$C_8$alkyl ether, $C_1$–$C_8$alkylthio, mono- or di-($C_1$–$C_8$alkyl)amino, mono- or di-($C_1$–$C_8$)-alkyl)sulfonamido, or mono- or di-($C_1$–$C_8$alkyl)carboxamido, each of which is optionally substituted with from 1 to 9 substituents independently selected from hydroxy, halogen, amino, cyano, nitro, $C_1$–$C_8$alkyl, halo$C_1$–$C_8$alkyl and mono- and di-($C_1$–$C_8$alkyl)amino; or
(iii) joined with $R_2$ to form a 5- to 7-member heterocyclic ring;

$R_2$ is:
(i) hydrogen, —C(=O)NH$_2$, —SO$_2$NH$_2$ or —COOH;
(ii) $C_1$–$C_8$alkyl, $C_2$–$C_8$alkenyl, $C_2$–$C_8$alkynyl, $C_1$–$C_8$alkoxy, $C_2$–$C_8$alkanoyl, $C_2$–$C_8$alkyl ether, $C_2$–$C_8$alkanoyloxy, $C_1$–$C_8$alkoxycarbonyl, $C_1$–$C_8$carbonate, $C_1$–$C_8$alkylthio, mono- or di-($C_1$–$C_8$alkyl)amino, $C_1$–$C_8$carbamate, mono- or di-($C_1$–$C_8$alkyl)sulfonamido or mono- or di-($C_1$–$C_8$alkyl)carboxamido, each of which is optionally substituted with from 1 to 9 substituents independently selected from hydroxy, halogen, amino, cyano, nitro, $C_1$–$C_8$alkyl and halo$C_1$–$C_8$alkyl; or
(iii) joined with $R_1$ to form a 5- to 7-member heterocyclic ring;

$R_3$ represents 0 to 4 substituents, wherein each substituent is linked to a carbon atom at A, B, E or D, and each substituent is independently selected from:
(i) halogen, hydroxy, amino, cyano, nitro, —C(=O) NH$_2$, —SO$_2$NH$_2$ and —COOH; and
(ii) $C_1$–$C_8$alkyl, $C_2$–$C_8$alkenyl, $C_2$–$C_8$alkynyl, $C_1$–$C_8$alkoxy, $C_2$–$C_8$alkanoyl; $C_2$–$C_8$alkanoyloxy, $C_1$–$C_8$alkoxycarbonyl, $C_1$–$C_8$carbonate, $C_1$–$C_8$alkylthio, mono- and di-($C_1$–$C_8$alkyl)amino, $C_1$–$C_8$carbamate, mono- and di-($C_1$–$C_8$alkyl) sulfonamido, and mono- and di-($C_1$–$C_8$alkyl) carboxamido, each of which is optionally substituted with from 1 to 9 secondary substituents independently selected from hydroxy, halogen, amino, cyano, nitro, $C_1$–$C_8$alkyl and halo$C_1$–$C_8$alkyl;

L is $C_1$–$C_3$alkyl;

Q is $C_0$–$C_3$ alkyl, $C_2$–$C_3$ alkenyl or $C_2$–$C_3$ alkynyl;

$R_6$ and $R_7$: jointly with the nitrogen atom to which they are bound form a 6-membered heterocyclic ring optionally substituted with from 1 to 3 substituents independently selected from hydroxy, halogen, amino, cyano, nitro, $C_1$–$C_8$alkyl, halo$C_1$–$C_8$alkyl, $C_1$–$C_8$alkoxy and halo$C_1$–$C_8$alkoxy;

X represents $C_0$–$C_3$alkyl, $C_2$–$C_3$alkenyl, $C_2$–$C_3$alkynyl, $C_1$–$C_3$alkoxy, $C_1$–$C_3$alkoxycarbonyl or $C_1$–$C_3$alkylthio;

$R_5$ represents an aromatic carbocyclic group having 1 or 3 fused or pendant rings, each ring containing from 5 to 8 ring members, wherein the aromatic group is optionally substituted by from 1 to 9 substituents that are independently selected from:
(i) hydrogen, halogen, hydroxy, amino, cyano, nitro, —C(=O)NH$_2$, —SO$_2$NH$_2$ and —COOH; and
(ii) $C_1$–$C_8$alkyl, $C_2$–$C_8$alkenyl, $C_2$–$C_8$alkynyl, $C_1$–$C_8$alkoxy, $C_2$–$C_8$alkanoyl, $C_2$–$C_8$alkanoyloxy, $C_1$–$C_8$alkoxycarbonyl, $C_1$–$C_8$carbonate, $C_1$–$C_8$alkylthio, mono- and di-($C_1$–$C_8$alkyl)amino, $C_1$–$C_8$carbamate, mono- and di-($C_1$–$C_8$alkyl) sulfonamido, and mono and di-($C_1$–$C_8$alkyl) carboxamido, each of which is optionally substituted with from 1 to 5 secondary substituents independently selected from hydroxy, halogen, amino, cyano, nitro, $C_1$–$C_8$alkyl and halo$C_1$–$C_8$alkyl; and Y is —(C=O)—, —C(=S)—, —S(=O)— or —(SO$_2$)—;

wherein the compound exhibits a $K_i$ of 500 nanomolar or less in an MCH receptor ligand binding assay, and wherein the compound exhibits a $K_i$ of greater than 1 micromolar in a human bradykinin B$_2$ receptor ligand binding assay.

2. A compound according to claim 1, wherein the compound has the formula:

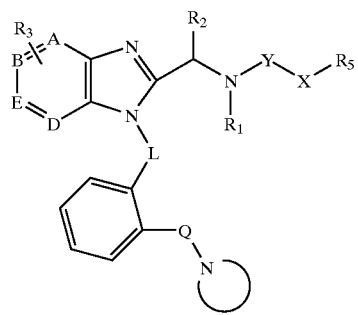

wherein

is a 6- membered heterocyclic ring, linked to Q via a nitrogen atom, and optionally substituted with from 1 to 3 substituents selected from hydroxy, halogen, amino, cyano, nitro, $C_1$–$C_6$alkyl, halo$C_1$–$C_6$alkyl, $C_1$–$C_6$alkoxy, and halo$C_1$–$C_6$alkoxy.

3. A compound according to claim 2, wherein

is piperidinyl, methyl-piperidinyl, morpholinyl, or piperazinyl, optionally substituted with from 1 to 3 substituents selected from hydroxy, halogen, amino, cyano, nitro, $C_1$–$C_8$alkyl and halo$C_1$–$C_8$alkyl.

4. A compound according to claim 3, wherein Q is —CH$_2$—.

5. A compound according to claim 4, wherein L is —CH$_2$— and wherein

is piperidinyl.

6. A compound according to claim 1, wherein $R_5$ is a 5- to 10-membered mono- or bicyclic aromatic group, optionally substituted by from 1 to 3 substituents selected from halogen, $C_1$–$C_6$alkyl, halo$C_1$–$C_6$alkyl, $C_1$–$C_6$alkoxy, halo$C_1$–$C_6$alkoxy and $C_1$–$C_6$alkylthio.

7. A compound according to claim 6, wherein $R_5$ is, methylphenyl, 2,3- or 2,5-difluorophenyl, 4-methylsulfanylphenyl, 2-ethoxyphenyl, 2-chloro-5-trifluoromethylphenyl, 1-naphthyl, 8-bromo-1-naphthyl, 3-fluoro-4-methoxyphenyl, 2-methyl-5-fluorophenyl, 4-chlorophenyl, or 2,5- or 2,6-dichlorophenyl.

8. A compound according to claim 1, wherein $R_1$ is $C_1$–$C_6$alkyl, $C_2$–$C_6$alkyl ether or di($C_1$–$C_6$alkyl)amino ($C_1$–$C_6$alkyl).

9. A compound according to claim 8, wherein $R_1$ is propyl, n-butyl, 3-methyl-butyl, isobutyl or cyclopropylmethyl.

10. A compound according to claim 1, wherein $R_2$ is H, $C_1$–$C_6$alkyl, $C_1$–$C_6$alkoxy, halo$C_1$–$C_6$alkyl, halo$C_1$–$C_6$alkoxy, or $C_2$–$C_6$alkyl ether.

11. A compound according to claim 1, wherein the compound is selected from:
(2,3-Difluoro-phenyl)-{2-[1-(2-piperidin-1-ylmethyl-benzyl)-1H-benzoimidazol-2-yl]-pyrrolidin-1-yl}-methanone;
(2,3-Difluoro-phenyl)-{2-[1-(2-piperidin-1-ylmethyl-benzyl)-1H-benzoimidazol-2-yl]-piperidin-1-yl}-methanone;
2,3-Difluoro-N-(3-methoxy-propyl)-N-[1-(2-piperidin-1-ylmethyl-benzyl)-1H-benzoimidazol-2-ylmethyl]-benzamide;
2,3-Difluoro-N-[1-(2-piperidin-1-ylmethyl-benzyl)-1H-benzoimidazol-2-ylmethyl]-N-propyl-benzamide;
2,3-Difluoro-N-isobutyl-N-[1-(2-piperidin-1-ylmethyl-benzyl)-1H-benzoimidazol-2-ylmethyl]-benzamide;
2,3-Difluoro-N-methyl-N-[1-(2-piperidin-1-ylmethyl-benzyl)-1H-benzoimidazol-2-ylmethyl]-benzamide;
2,4-Difluoro-N-isobutyl-N-[1-(2-piperidin-1-ylmethyl-benzyl)-1H-benzoimidazol-2-ylmethyl]-benzamide;
2-Bromo-N-isobutyl-4,5-dimethoxy-N-[1-(2-piperidin-1-ylmethyl-benzyl)-1H-benzoimidazol-2-ylmethyl]-benzamide;
2-Chloro-3,4-dimethoxy-N-(3-methyl-butyl)-N-[1-(2-morpholin-4-ylmethyl-benzyl)-1H-benzoimidazol-2-ylmethyl]-benzamide;

2-Chloro-3,4-dimethoxy-N-(3-methyl-butyl)-N-[1-(2-piperidin-1-ylmethyl-benzyl)-1H-benzoimidazol-2-ylmethyl]-benzamide;

2-Chloro-3,4-dimethoxy-N-(3-methyl-butyl)-N-{1-[2-(4-methyl-piperazin-1-ylmethyl)-benzyl]-1H-benzoimidazol-2-ylmethyl}-benzamide;

2-Chloro-3,4-dimethoxy-N-(3-methyl-butyl)-N-{1-[2-(4-methyl-piperidin-1-ylmethyl)-benzyl]-1H-benzoimidazol-2-ylmethyl}-benzamide;

2-Chloro-4,5-dimethoxy-N-(3-methylbutyl)-N-[1-(2-piperidin-1-ylmethyl-benzyl)-1H-benzoimidazol-2-ylmethyl}-benzamide;

2-Chloro-N-{1-[2-(3,3-dimethyl-piperidin-1-ylmethyl)-benzyl]-1H-benzoimidazol-2-ylmethyl}-3,4-dimethoxy-N-(3-methyl-butyl)-benzamide;

2-Chloro-N-isobutyl-N-[1-(2-piperidin-1-ylmethyl-benzyl)-1H-benzoimidazol-2-ylmethyl]-5-trifluoromethyl-benzamide;

2-Chloro-N-isobutyl-N-[1-(2-piperidin-1-ylmethyl-benzyl)-1H-benzoimidazol-2-ylmethyl]-5-trifluoromethyl-benzamide;

2-ethoxy-N-(3-methylbutyl)-N-[1-(2-piperidin-1-ylmethyl-benzyl)-1H-benzoimidazol-2-ylmethyl]-benzamide;

2-phenyl-cyclopropanecarboxylic acid (3-methyl-butyl)-[1-(2-piperidin-1-ylmethyl-benzyl)-1H-benzoimidazol-2-ylmethyl]-amide;

3-(2,3-difluorophenyl)-N-isobutyl-N-[1-(2-piperdin-1-ylmethyl-benzyl)-1H-benzoimidazol-2-ylmethyl]-acrylamide;

3-(2,3-Difluoro-phenyl)-N-isopropyl-N-[1-(2-piperidin-1-ylmethyl-benzyl)-1H-benzoimidazol-2-ylmethyl]-acrylamide;

4-Bromo-N-butyl-N-[1-(2-piperidin-1-ylmethyl-benzyl)-1H-benzoimidazol-2-ylmethyl]-benzamide;

4-Chloro-N-isobutyl-N-[1-(2-piperidin-1-ylmethyl-benzyl)-1H-benzoimidazol-2-ylmethyl]-benzamide;

5-Chloro-thiophene-2-sulfonic acid butyl-[1-(2-piperidin-1-ylmethyl-benzyl)-1H-benzoimidazol-2-ylmethyl]-amide;

8-bromo-naphthalene-1-carboxylic acid butyl-[1-(2-piperidin-1-ylmethyl-benzyl)-1H-benzoimidazol-2-ylmethyl]-amide;

8-Iodo-naphthalene-1-carboxylic acid butyl-[1-(2-piperidin-1-ylmethyl-benzyl)-1H-benzoimidazol-2-ylmethyl]-amide;

N-(3-Methyl-butyl)-N-[1-(2-piperidin-1-ylmethyl-benzyl)-1H-benzoimidazol-2-ylmethyl]-4-trifluoromethoxy-benzamide;

Naphthalene-1-carboxylic acid isobutyl-[1-(2-piperidin-1-ylmethyl-benzyl)-1H-benzoimidazol-2-ylmethyl]-amide;

N-butyl-2,3-difluoro-N-[1-(2-piperdin-1-ylmethyl-benzyl)-1H-benzoimidazol-2-ylmethyl]-benzamide;

N-Butyl-2,3-difluoro-N-[1-(2-piperidin-1-ylmethyl-benzyl)-5-trifluoromethyl-1H-benzoimidazol-2-ylmethyl]-benzamide;

N-Butyl-2,3-difluoro-N-{1-[1-(2-piperidin-1-ylmethyl-benzyl)-1H-benzoimidazol-2-yl]-ethyl}-benzamide;

N-Butyl-2,3-difluoro-N-{1-[1-(2-piperidin-1-ylmethyl-phenyl)-ethyl]-1H-benzoimidazol-2-ylmethyl}-benzamide;

N-Butyl-2,4-difluoro-N-[1-(2-piperidin-1-ylmethyl-benzyl)-1H-benzoimidazol-2-ylmethyl]-benzamide;

N-butyl-2,5-dichloro-N-[1-(2-piperidin-1-ylmethyl-benzyl)-1H-benzoimidazol-2-ylmethyl]-benzamide;

N-butyl-2-chloro-3,4-dimethoxy-N-[1-(2-piperidin-1-ylmethyl-benzyl)-1H-benzoimidazol-2-ylmethyl]-benzamide;

N-Butyl-2-chloro-N-[1-(2-piperidin-1-ylmethyl-benzyl)-1H-benzoimidazol-2-ylmethyl]-5-trifluoromethyl-benzamide;

N-Butyl-2-chloro-N-[1-(2-piperidin-1-ylmethyl-benzyl)-1H-benzoimidazol-2-ylmethyl]-5-trifluoromethyl-benzamide;

N-Butyl-2-methyl-5-fluoro-N-[1-(2-piperidin-1-ylmethyl-benzyl)-1H-benzoimidazol-2-ylmethyl]-benzamide;

N-Butyl-3-(2,3-difluoro-phenyl)-N-[1-(2-piperidin-1-ylmethyl-benzyl)-1H-benzoimidazol-2-ylmethyl]-acrylamide;

N-Butyl-3,4-difluoro-N-[1-(2-piperidin-1-ylmethyl-benzyl)-1H-benzoimidazol-2-ylmethyl]-benzamide;

N-Butyl-3-chloro-4-methoxy-N-[1-(2-piperidin-1-ylmethyl-benzyl)-1H-benzoimidazol-2-ylmethyl]-benzamide;

N-Butyl-3-fluoro-4-methoxy-N-[1-(2-piperidin-1-ylmethyl-benzyl)-1H-benzoimidazol-2-ylmethyl]-benzamide;

N-Butyl-3-fluoro-4-methyl-N-[1-(2-piperidin-1-ylmethyl-benzyl)-1H-benzoimidazol-2-ylmethyl]-benzamide;

N-Butyl-3-fluoro-4-methyl-N-[1-(2-piperidin-1-ylmethyl-benzyl)-1H-benzoimidazol-2-ylmethyl]-benzamide;

N-Butyl-3-fluoro-N-[1-(2-piperidin-1-ylmethyl-benzyl)-1H-benzoimidazol-2-ylmethyl]-benzamide;

N-butyl-4-chloro-N-[1-(2-piperidin-1-ylmethyl-benzyl)-1H-benzoimidazol-2-ylmethyl]-benzamide;

N-Butyl-4-chloro-N-[1-(2-piperidin-1-ylmethyl-benzyl)-1H-benzoimidazol-2-ylmethyl]-benzenesulfonamide;

N-Butyl-4-cyano-N-[1-(2-piperidin-1-ylmethyl-benzyl)-1H-benzoimidazol-2ylmethyl]-benzamide;

N-Butyl-4-ethoxy-N-[1-(2-piperidin-1-ylmethyl-benzyl)-1H-benzoimidazol-2-ylmethyl]-benzamide;

N-Butyl-4-ethylaminomethyl-N-[1-(2-piperidin-1-ylmethyl-benzyl)-1H-benzoimidazol-2-ylmethyl]-benzamide;

N-Butyl-4-fluoro-N-[1-(2-piperidin-1-ylmethyl-benzyl)-1H-benzoimidazol-2-ylmethyl]-benzenesulfonamide;

N-Butyl-4-methanesulfonyl-N-[1-(2-piperidin-1-ylmethyl-benzyl)-1H-benzoimidazol-2-ylmethyl]-benzamide;

N-Butyl-4-methylaminomethyl-N-[1-(2-piperidin-1-ylmethyl-benzyl)-1H-benzoimidazol-2-ylmethyl]-benzamide;

N-butyl-4-methylsulfanyl-N-[1-(2-piperidin-1-ylmethyl-benzyl)-1H-benzoimidazol-2-ylmethyl]-benzamide;

N-Butyl-4-methylsulfanyl-N-[1-(2-piperidin-1-ylmethyl-benzyl)-1H-benzoimidazol-2-ylmethyl]-benzamide;

N-Butyl-4-morpholin-4-ylmethyl-N-[1-(2-piperidin-1-ylmethyl-benzyl)-1H-benzoimidazol-2-ylmethyl]-benzamide;

N-Butyl-4-pentyloxy-N-[1-(2-piperidin-1-ylmethyl-benzyl)-1H-benzoimidazol-2-ylmethyl]-benzamide;

N-Butyl-4-piperidin-1-ylmethyl-N-[1-(2-piperidin-1-ylmethyl-benzyl)-1H-benzoimidazol-2-ylmethyl]-benzamide;

N-Butyl-5-fluoro-2-methyl-N-[1-(2-piperidin-1-ylmethyl-benzyl)-1H-benzoimidazol-2-ylmethyl]-benzenesulfonamide;

N-Butyl-N-[1-(2-piperidin-1-ylmethyl-benzyl)-1H-benzoimidazol-2-ylmethyl]-3-o-tolyl-acrylamide;

N-Butyl-N-[1-(2-piperidin-1-ylmethyl-benzyl)-1H-benzoimidazol-2-yl methyl]-4-trifluoromethylsulfanyl-benzamide;

N-Butyl-N-[1-(2-piperidin-1-ylmethyl-benzyl)-1H-benzoimidazol-2-yl methyl]-benzenesulfonamide;

N-Butyl-N-[1-(2-piperidin-1-ylmethyl-benzyl)-1H-benzoimidazol-2-ylmethyl]-4-pyrrolidin-1-ylmethyl-benzamide;

N-Butyl-N-[1-(2-piperidin-1-ylmethyl-benzyl)-1H-benzoimidazol-2-ylmethyl]-4-propylaminomethyl-benzamide;

N-Butyl-N-[5-cyano-1-(2-piperidin-1-ylmethyl-benzyl)-1H-benzoimidazol-2-ylmethyl]-2,3-difluoro-benzamide;

N-cyclopropylmethyl-2,3-difluoro-N-[1-(2-piperdin-1-ylmethyl-benzyl)-1H-benzoimidazol-2-ylmethyl]-benzamide;

N-cyclopropylmethyl-4-methylsulfanyl-N-[1-(2-piperidin-1-ylmethyl-benzyl)-1H-benzoimidazol-2-ylmethyl]-benzamide;

N-Cyclopropylmethyl-N-[1-(2-piperidin-1-ylmethyl-benzyl)-1H-benzoimidazol-2-ylmethyl]-4-trifluoromethylsulfanyl-benzamide;

N-Ethyl-2,3-difluoro-N-[1-(2-piperidin-1-ylmethyl-benzyl)-1H-benzoimidazol-2-ylmethyl]-benzamide;

N-isobutyl-3-naphthalen-1-yl-N-[1-(2-piperdin-1-ylmethyl-benzyl)-1H-benzoimidazol-2-ylmethyl]-acrylamide;

N-Isobutyl-4-pentyloxy-N-[1-(2-piperidin-1-ylmethyl-benzyl)-1H-benzoimidazol-2-ylmethyl]-benzamide;

N-isobutyl-N-[1-(2-piperdin-1-ylmethyl-benzyl)-1H-benzoimidazol-2-ylmethyl]-3-o-tolyl-acrylamide;

N-Isobutyl-N-[1-(2-piperidin-1-ylmethyl-benzyl)-1H-benzoimidazol-2-ylmethyl]-benzamide;

N-Isopropyl-N-[1-(2-piperidin-1-ylmethyl-benzyl)-1H-benzoimidazol-2-ylmethyl]-benzamide;

N-Isopropyl-N-[1-(2-piperidin-1-ylmethyl-benzyl)-1H-benzoimidazol-2-ylmethyl]-3-o-tolyl-acrylamide;

N-pentyl-3-(2,6-dichloro-phenyl)-N-[1-(2-piperidin-1-ylmethyl-benzyl)-1H-benzoimidazol-2-ylmethyl]-acrylamide; and N-propyl-2,3-difluoro-N-[1-(2-piperidin-1-ylmethyl-benzyl)-1H-benzoimidazol-2-ylmethyl]-benzamide.

12. A compound according to claim 1, wherein the compound exhibits a $K_i$ of 100 nanomolar or less in an MCH receptor ligand binding assay.

13. A compound according to claim 1, wherein the compound exhibits a $K_i$ of 10 nanomolar or less in an MCH receptor ligand binding assay.

14. A pharmaceutical composition comprising a compound according to claim 1 in combination with a physiologically acceptable carrier or excipient.

15. A compound according to claim 5, wherein:

is piperidinyl, optionally substituted with 1 or 2 substituents independently chosen from hydroxy, halogen, amino, cyano, nitro, $C_1$–$C_8$alkyl and halo$C_1$–$C_8$alkyl;

Q is —CH$_2$—;

L is —CH$_2$—;

X is $C_0$–$C_3$alkyl or $C_2$–$C_3$alkenyl;

Y is —(C=O)— or —SO$_2$—;

R$_2$ is hydrogen; and

R$_1$ is $C_1$–$C_6$alkyl.

16. A compound according to claim 6, wherein R$_5$ is phenyl or naphthyl, each of which is optionally substituted with from 1 to 3 substituents selected from halogen, $C_1$–$C_6$alkyl, halo$C_1$–$C_6$alkyl, $C_1$–$C_6$, alkoxy, halo$C_1$–$C_6$alkoxy and $C_1$–$C_6$alkylthio.

* * * * *